US007016045B2

(12) United States Patent
Kwon

(10) Patent No.: US 7,016,045 B2
(45) Date of Patent: Mar. 21, 2006

(54) VIDEO CAMERA-BASED VISIBILITY MEASUREMENT SYSTEM

(75) Inventor: Taek Mu Kwon, Duluth, MN (US)

(73) Assignee: Regents of the University of Minnesota, Minneapoliis, MN (US)

( * ) Notice: Subject to any disclaimer, the term of this patent is extended or adjusted under 35 U.S.C. 154(b) by 429 days.

(21) Appl. No.: 10/346,796

(22) Filed: Jan. 13, 2003

(65) Prior Publication Data

US 2003/0197867 A1 Oct. 23, 2003

Related U.S. Application Data

(63) Continuation-in-part of application No. 10/330,831, filed on Dec. 26, 2002, now Pat. No. 6,853,453, which is a continuation of application No. 09/267,035, filed on Mar. 12, 1999, now abandoned.
(60) Provisional application No. 60/347,410, filed on Jan. 11, 2002.

(51) Int. Cl.
*G01N 21/61* (2006.01)

(52) U.S. Cl. ..................................................... 356/437

(58) Field of Classification Search .................. 356/437
See application file for complete search history.

(56) References Cited

U.S. PATENT DOCUMENTS

| | | | |
|---|---|---|---|
| 2,198,971 A | | 4/1940 | Neufeld |
| 3,694,936 A | | 10/1972 | Ling et al. |
| 4,200,398 A | | 4/1980 | Persson et al. |
| 4,216,498 A | * | 8/1980 | Evans et al. ............. 356/435 |
| 4,921,349 A | * | 5/1990 | Richards .................. 356/438 |
| 5,987,152 A | | 11/1999 | Weisser |
| 6,085,152 A | * | 7/2000 | Doerfel .................... 702/3 |
| 6,128,088 A | | 10/2000 | Nishiwaki |

FOREIGN PATENT DOCUMENTS

DE 3801368 A1 7/1989

OTHER PUBLICATIONS

Brooks, C.E.P. et al., *Glossary of Meteorology*, American Meteorological Society, Boston, Massachusetts, 7 pages (1959).
Duntley, S., "The Reduction of Apparent Contrast by the Atmosphere," *Journal of the Optical Society of America*, vol. 38, No. 2, pp. 179–191 (Feb. 1948).
Gonzalez, R. C. et al., "Digital Image Processing, Chapter 1 and Digital Image Fundamentals, Chapter 2," pp. 1–19 and 21–52 (Jun. 1992).
Ortega, J.M. et al., "Minimization Methods, Chapter 8," *Interative Solution of Nonlinear Equations in Several Variables*, pp. 240–278 (1970).
Knowles Middleton, W.E., *Vision Through the Atmosphere*, Table of Contents (pp. vii and viii), Chapter 1 (pp. 3–17), Chapters 4–6(pp. 60–136), Chapter 9 (pp. 175–214) (1952).
Takeuchi, M., "Vertical Profile and Horizontal Increase of Drift–Snow Transport," *Journal of Glaciology*, vol. 26, No. 94, pp. 481–492 (1980).
U.S. Department of Transportation, Federal Highway Administration, "Environmental Sensor Systems for Safe Traffic Operations," pp. 2 cover pages, i–x, and 1–150 (Oct. 1995).
Kwon, T.M., "An Automatic Visibility Measurement System Based on Video Cameras," 2 cover sheets, i–v, and 1–62 (Sep. 1998).

* cited by examiner

*Primary Examiner*—Richard A. Rosenberger
(74) *Attorney, Agent, or Firm*—Merchant & Gould P.C.

(57) ABSTRACT

A visibility measurement system that computes relative visibility by comparing an images of an environment against a benchmark image. A sensing device receives an image and a digital conversion system maps the image into a two-dimensional data array. A processor converts the digital data to a value that represents visibility by identifying a region in the image that has a uniform distance from the sensing device over time, computing a benchmark visibility index for the region as a summation of measurable visual characteristics that influence visibility in the region under a benchmark environmental condition, computing a second visibility index for a second environmental condition, and computing a relative visibility value as the ration of the second visibility index in relation to the benchmark visibility index.

22 Claims, 15 Drawing Sheets

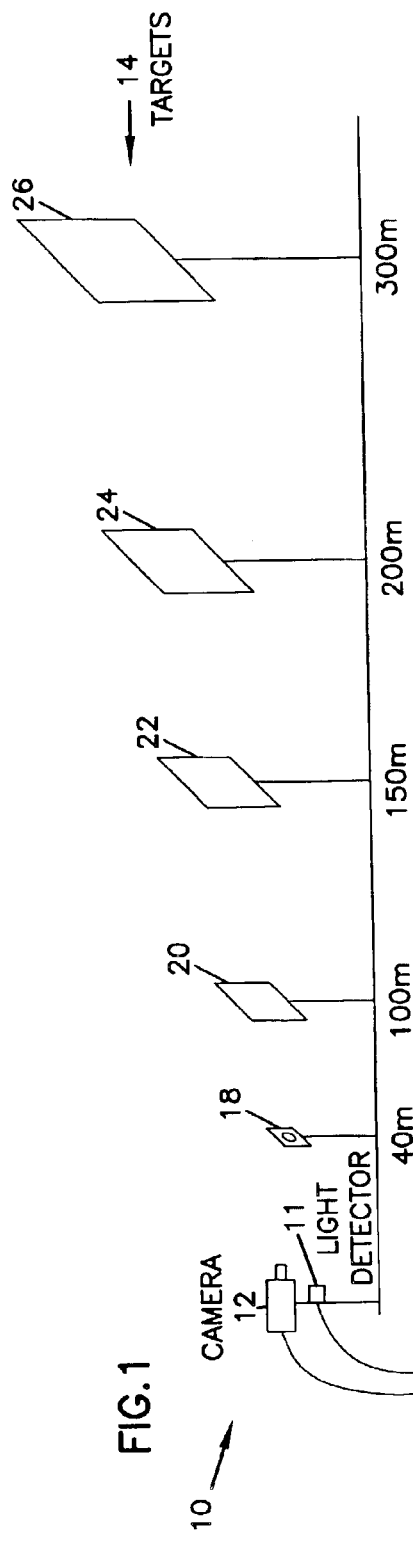
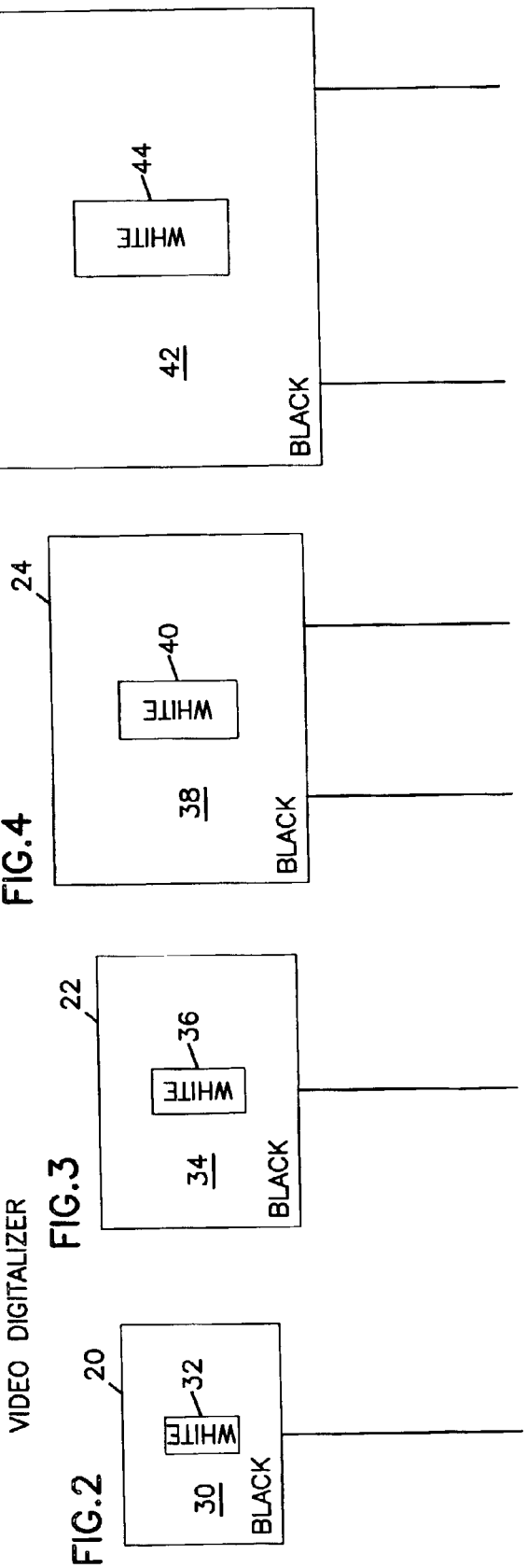

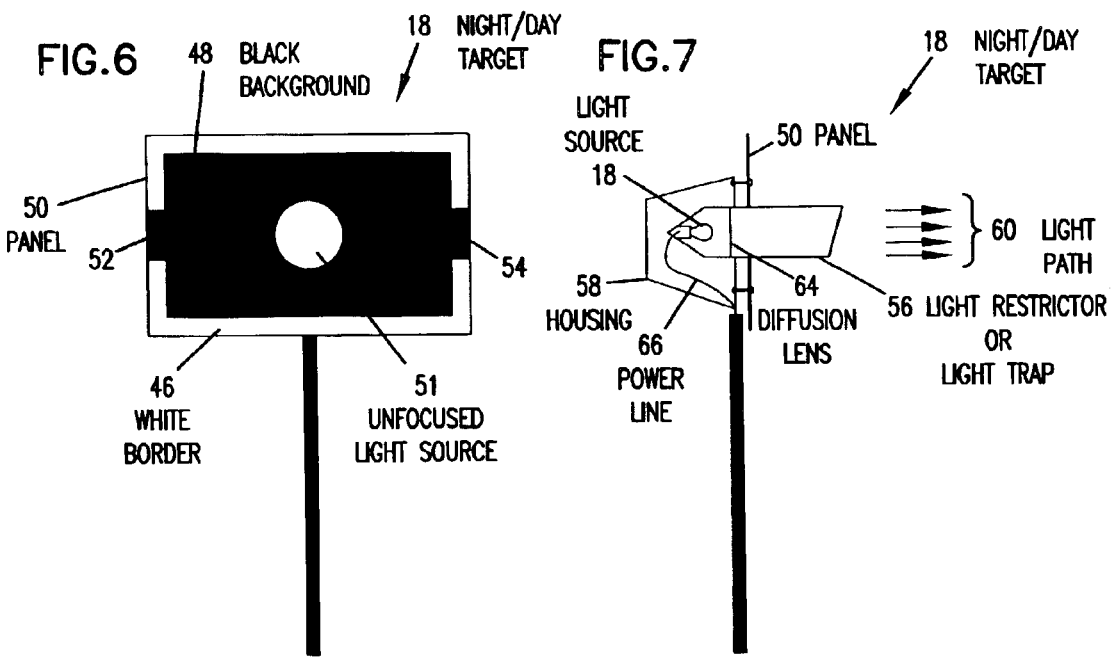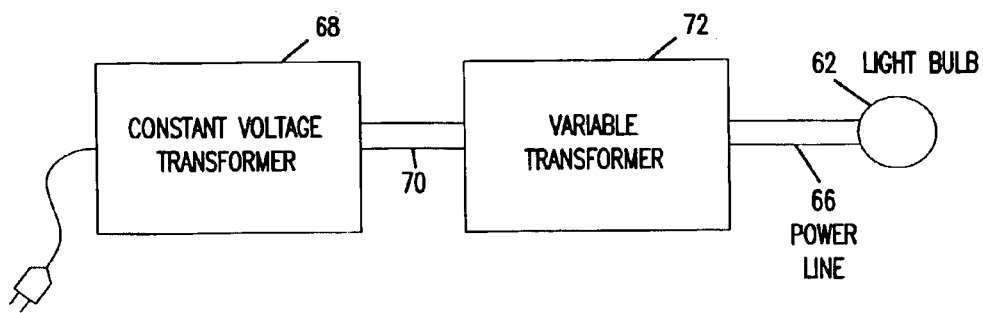

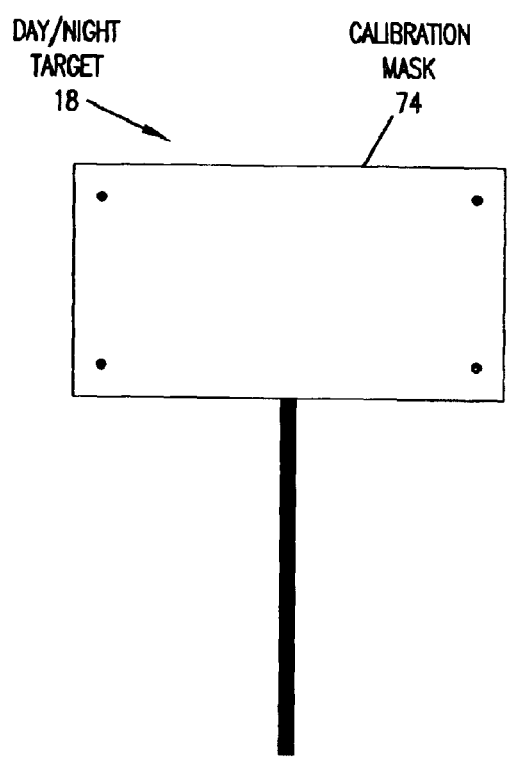
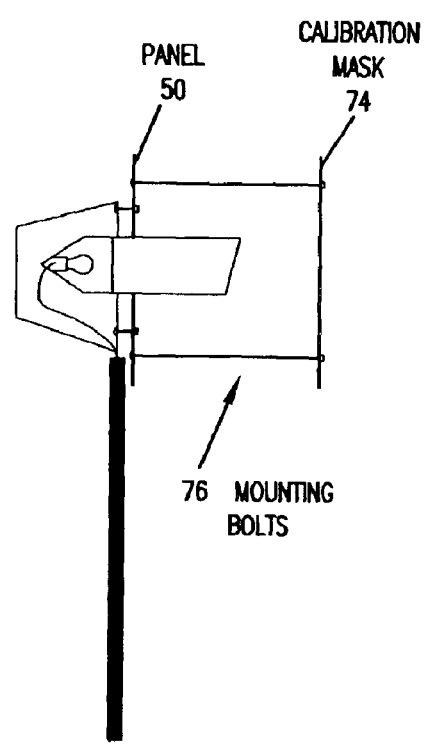

AN EXAMPLE REGION SELECTION OF HIGHWAY

SIDE VIEW OF GEOMETRICAL RELATION

TOP VIEW OF GEOMEYTICAL RELATION

VIDEO CAMERA-BASED VISIBILITY MEASUREMENT SYSTEM

CROSS REFERENCE TO RELATED APPLICATIONS

This application is a Continuation-in-Part of Ser. No. 10/330,831, filed Dec. 26, 2002, now U.S. Pat. No. 6,853,453 which is a Continuation of application Ser. No. 09/267,035, filed Mar. 12, 1999 (now abandoned). Priority is also claimed to Provisional application Ser. No. 60/347,410, filed Jan. 11, 2002.

BACKGROUND OF THE INVENTION

A. Field of the Invention

The present invention pertains generally to automated methods of measuring atmospheric visibility and, more particularly, to a video camera-based system for measuring atmospheric visibility.

B. Description of the Background

Visibility conditions are affected by the structure and elements of the atmosphere, such as fog, snow, wind, dust, and other adverse conditions. Visibility has been defined as the greatest distance at which an object of specified characteristics can be seeing and detected by the naked eye. See *American Meteorological Society*, Glossary of Meteorology, 1989, and W. E. Knowles Middleton, *Vision Through Atmosphere*, 1968, University of Toronto Press. Atmospheric visibility is normally expressed in distance, such as meters or yards, or at greater distances in kilometers or miles. Atmospheric visibility at night is determined by measuring the distance from a point of light of a given intensity to a point where the light source is just detectable by the human eye. See *American Meteorological Society* and W. E. Knowles Middleton, supra. Currently, most visibility measurement instruments are based on the principle of measuring forward or backward light scattering effects.

As light is scattered by atmospheric particles, scattered light meters record the visibility. There are a number of problems, however, with measuring visibility using scattered light meters (SLMs). First, light scattering by atmospheric particles such as atmospheric moisture is only one of the effects that reduce visibility in the atmosphere. For example, absorption or obscuration by large particulate matter such as snow, dust, etc. can have a much greater effect on atmospheric visibility than simple light scattering of smaller particles, such as atmospheric moisture that causes fog. Hence, light scattering of smaller particles only contributes partially to atmospheric visibility effects.

Additionally, SLMs typically only measure the light scattering effects of a small region of a few cubic inches located adjacent the SLM. If the local region adjacent the SLM deviates from the overall visibility, such as the visibility along a road at a distance of up to 300 meters, the SLM will report a very large error. Local regions of fog, blowing snow, local dust storms and other effects can cause the visibility to vary drastically from one spot to another. Hence, SLMs are prone to providing incorrect readings of visibility in adverse conditions.

While SLMs provide a fairly accurate measure of light scattering, and hence visibility under conditions of fog where atmospheric moisture is the primary contributing factor for low visibility, SLMs may provide a high margin of error for visibility measurements under rain and snow conditions for the reasons as set forth above. One of the reasons is that there is a less significant correlation between atmospheric visibility and the light scattering effect under rain and snow conditions. Additionally, the light scattering effect varies with different types of atmospheric particles. In order for SLMs to correctly measure visibility, the SLMs need to recognize both the types and size of particles and self-calibrate to adjust the measurement of atmospheric visibility according to the different scattering properties of atmospheric particles to provide a proper measurement. The ability to determine the types and sizes of particles present in the atmosphere, as well as the ability to self-calibrate an SLM according to the types and sizes of particles detected, would greatly increase the cost of the SLM and would most likely provide results that are still prone to errors.

Hence, atmospheric visibility that is perceived by the human eye can often be very different from the visual range measured by SLMs due to the basic operating principles of the SLM. As pointed out above, SLMs only measure one physical property of the atmosphere, and only measure that property in a small region that is located near the SLM. Additionally, SLMs do not provide an easy way to verify the correctness of the visibility that is reported by the SLM. Since visibility is often used to make critical decisions in transportation applications, such as road closures or speed limit decisions, it is vitally important that such decisions be verified.

Statistical reliability has been used as an alternative to verification in some instances. For example, several SLMs may be installed in the area in which atmospheric visibility is to be measured to increase the statistical reliability of the measurements that are made. Since SLMs are very expensive, this greatly increases the cost, and the SLMs still suffer from the inherent problems indicated above. Moreover, SLMs require a high degree of precision in the alignment of the transmitter and receiver optics which additionally adds to the cost of the SLM systems.

It is against this background, and the limitations and problems associated therewith, that the present invention has been developed.

SUMMARY OF THE INVENTION

The present invention provides a system that can accurately measure atmospheric visibility. In some respects, the measurement is similar to the manner in which the human eye perceives atmospheric visibility. The present invention can also utilize existing equipment that is used for other purposes, such as a video camera, which will additionally allow verification of automatic visibility measurements made by the system. Manual verification may be desired for example when important decisions need to be made regarding road closure or speed limit reductions.

Video cameras record the three-dimensional environment (real-world) into two-dimensional data space by projecting the angle of view of the camera onto a flat two-dimensional array of sensors such as Charge Coupled Devices (CCD). As a result, the depth (or distance to object) information that exists in the three-dimensional environment, which is critically important for visibility measurement, is typically lost. Moreover, the resolution of each pixel is limited, resulting in a limited accuracy in the relationship between visibility and contrast of video images. These two factors tend to limit the accuracy of visibility measurements from video-based visibility measurement systems.

In one system, these limitations may be overcome by utilizing multiple targets with known distances and by interpolating the strength of contrasts or edges based on atmospheric physics principles to the distance to infinity, which creates an effect of virtual creation of constant contrasting targets of infinite amount using few known targets. As a result, the lost depth or distance information of constant contrasting objects may be recovered through just few known targets, from which visibility, which is a distance measurement to an extinction point, may be accurately measured. This approach produces more accurate visibility measurement results as more targets are available. In one embodiment, the system may include two or more contrasting targets positioned at increasing order of distances with increasing size, a video sensing system producing image data in a digital form, and a processor that converts the atmospheric condition of the environment seen by the camera into a numeric number that represents visibility.

In another embodiment, a system for measuring atmospheric visibility may include at least two targets having contrasting portions, a video detector that is aligned to detect the contrasting portions of the targets and that generates a signal indicative of contrast levels of the contrasting portions of the target, and a processor that generates a representative contrast number from the contrast levels detected for each target, and that generates a nonlinear curve based on the representative contrast number detected for each target and the distance of each target from the video detector, and that generates a visibility number based on the slope of the exponential equation.

In another embodiment, a system for measuring atmospheric visibility in a predetermined region from a predetermined location may include a plurality of targets having visible contrasting portions, the plurality of targets disposed such that each target of the plurality of targets is disposed in the predetermined region at a distance from the predetermined location, an image detector disposed at the predetermined location that is aligned to view the plurality of targets and that generates an image signal that is indicative of contrast levels of the contrasting portions, and a processor that generates a visibility range measurement by determining a distance at which the contrast levels can just be distinguished based on the slope of an exponential curve that is representative of an average of the highest detected contrast levels for each of the targets versus the distance of the targets from the detector.

In another embodiment, a system for measuring atmospheric visibility in low light level conditions may include a light source that provides an unfocused column of light having a substantially spatially uniform intensity, an image detector that generates an image signal that has spatial intensity values of the light source that vary in accordance with an exponential curve having an exponential constant that is proportional to visibility, and a processor that generates a visibility measurement by determining the exponential constant from the spatial intensity values of the light source.

In another embodiment, an atmospheric visibility system may include a plurality of targets comprising a first target having contrasting portions of a first predetermined size that are visible by an image detector for use in the visibility system at a first predetermined distance from the image detector, and at least one additional target having contrasting portions of a second predetermined size at a second predetermined distance from the image detector, such that the first predetermined size at the first predetermined distance and the second predetermined size at the second predetermined distance appear substantially the same.

In another embodiment, a target of an atmospheric visibility system that can be used at night to detect atmospheric visibility may includes a light source that has a substantially uniform spatial intensity, and a light restrictor disposed to provide a defined source of light from the light source that has a contrasting edge.

In another embodiment, a method of measuring atmospheric visibility in a region measured from a predetermined location includes the steps of generating an image signal of a plurality of targets having contrasting portions, the plurality of targets disposed in the region at predetermined distances from the predetermined location, the image signal having intensity levels representative of the contrasting portions, generating representative contrast level signals for the plurality of targets from said intensity levels, generating an exponential curve that is indicative of said representative contrast level signal versus the distance of said plurality of targets from the predetermined location, and generating an atmospheric visibility measurement signal by locating a point on the exponential curve having a predetermined slope.

In another embodiment, a method of measuring atmospheric visibility in low light level conditions in a region measured from a predetermined location comprising the steps of, generating a source of light in the region at a predetermined distance from the predetermined location, the source of light having a substantially uniform spatial intensity that is sufficiently defined to produce a contrasting edge, generating an image signal that has spatial intensity values of the source of light that vary in accordance with an exponential curve having an exponential constant that is proportional to visibility, and generating a visibility measurement by determining the exponential constant and a proportionality constant for the exponential constant.

In another embodiment, visibility may be measured without the use of special known targets with constant contrasting parts. In some applications, it may be desirable to avoid setting up multiple of permanent targets for economic or space reasons. To address such concerns, a system may be constructed using only a video camera with a computing device that has a video digitizer (frame grabber). A processes may be used to ascertain relative visibility information from such system.

With this system, visibility may be quantified by consideration of "relative visibility" instead of absolute visibility. The computation of relative visibility (RV) is performed based on loss of visibility information relative to an image taken under an ideal weather condition, i.e., a clear day with no obstruction of view. This image is used as a benchmark against which images for other conditions are compared. While reference in this description is made to the "ideal condition," in practicality, it may not be possible to obtain an image under ideal conditions. While an image of an ideal condition would be desired, for the purpose of quantifying relative visibility, a reasonably high visibility benchmark condition will suffice.

RV is a normalized value between zero and one, representing the degree of how close the visual condition is to the ideal condition. RV becomes zero when no visual information is available, e.g., total white or black out conditions. RV becomes one when the present condition is identical to or above to the ideal reference condition. As the visual condition improves (or moves) towards the ideal condition, RV increases. Since the value of RV is between zero and one, it may also be expressed as percentage. This percentage information has a direct one-to-one relation to visibility expressed in meters.

In one embodiment, a video camera is mounted on a fixed location such as on a pole, so that it always sees the same scene. Preferably, the objects seen by the camera are located at various distances from the camera so that varying degree of visibility influences the clarity of object in the images. This can typically be achieved by positioning the camera so that horizon is visible from the camera view. In this configuration, objects in the image are arranged with varying unknown distances from the camera. Computing visibility from randomly arranged objects at unknown distances complicates the computation of visibility.

In another embodiment, a visibility measurement system includes an image sensing device for sensing at least two images of an environment, a digital conversion system that maps the image of environment into two-dimensional data array, and a processor. The processor converts the digital data to a value that represents visibility by identifying a region in the image that has a uniform distance from the sensing device over time, and computing a benchmark visibility index for the region as a summation of measurable visual characteristics that influence visibility in the region under a benchmark environmental condition. The processor also computes a second visibility index for a second environmental condition, and computes a relative visibility value as the ration of the second visibility index in relation to the benchmark visibility index. The visibility index is a function of clarity of objects in the image, the average luminance of the image, and the average contrast of the image.

BRIEF DESCRIPTION OF THE DRAWINGS

FIG. 1 is a schematic illustration of one implementation of the present invention.

FIGS. 2–5 illustrate daylight targets that can be used with the present invention.

FIG. 6 is a front view of a night target that can be used with the present invention.

FIG. 7 is a side view of a night target that can be used with the present invention.

FIG. 8 is a schematic block diagram of a power supply that can be used with the light source of the present invention.

FIG. 9 is a front view of the night target that has a calibration mask mounted on its front portion.

FIG. 10 is a side view of the night target that has a calibration mask mounted on its front portion.

DETAILED DESCRIPTION OF THE PREFERRED EMBODIMENT

Figure 11:
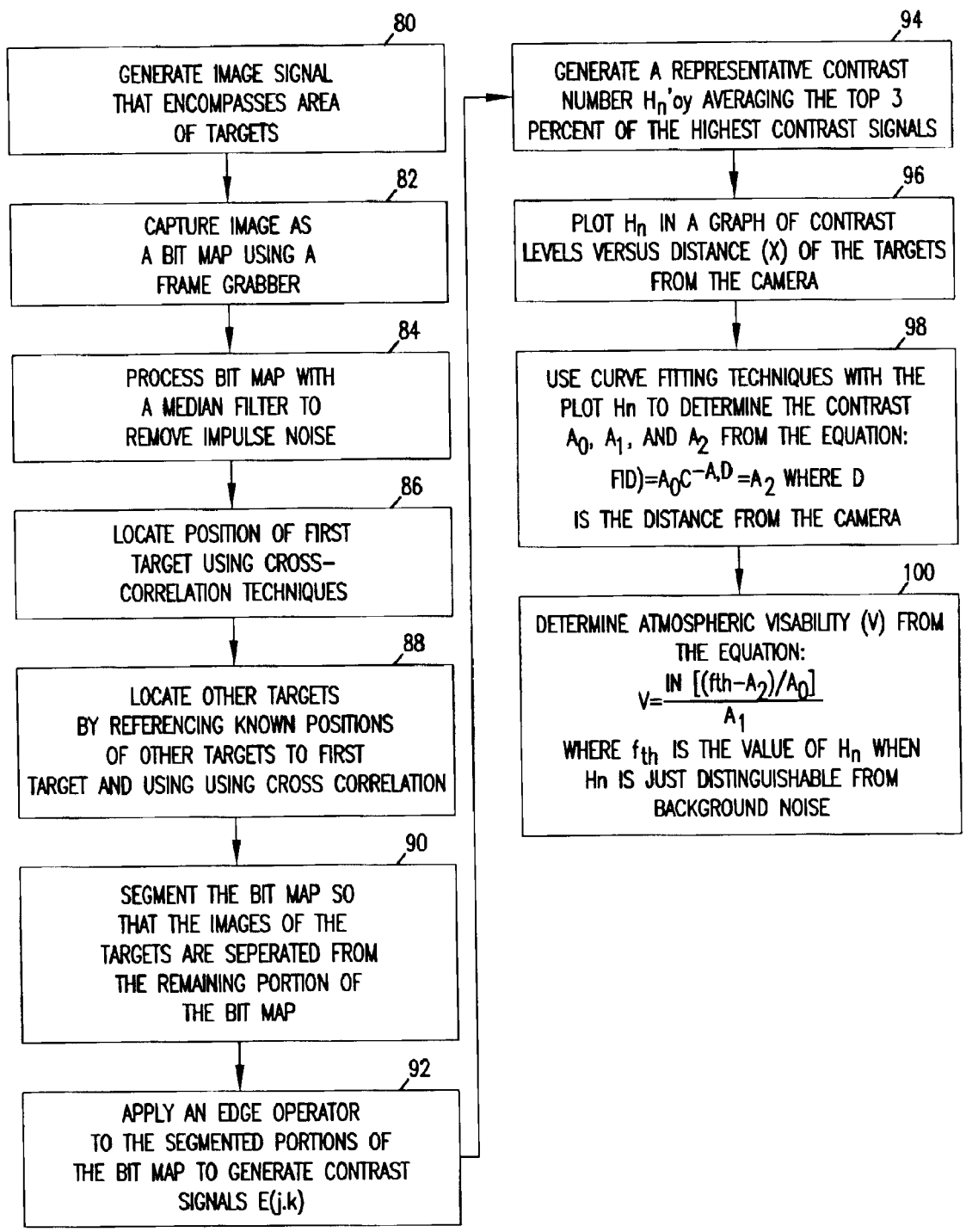
FIG. 11 is a flow diagram of the steps performed to measure atmospheric visibility during daylight.

Visibility may be measured using a video camera and a computer system. A series of targets may be used to measure visibility directly. Alternatively, visibility may be measured without specialized targets by computing a relative visibility from images of objects in view of a video camera. Systems using each of these techniques are described in detail below.

Relative visibility may be considered to be analogous to the relative humidity. Humidity is more accurately represented by measuring it relative to 100% humidity for a given temperature. In a similar manner, the visibility is dependent upon not just atmospheric conditions, but also the contrasts of the objects available from the scene viewed by the camera or human eye. More specifically, under the same atmospheric conditions, a location with higher contrasts such as an urban area with many buildings will have higher absolute visibility than a location with lower contrasts such as ocean. Essentially, visibility is a measurement of opacity in the visual path, and the degree of opacity is dependent not only on the air thickness or density but also the strength of the object contrasts behind.

Target-based Systems

In some situations, it may be desirable to measure visibility using a series of targets. FIG. 1 is a schematic illustration of a system 10 in which one embodiment the present invention can be implemented. As shown in FIG. 1, a camera such as a video camera or digital camera is aligned to view a series of targets 14 in a region in which measurement of atmospheric visibility is desired. Camera 12 can comprise any desired detector device that is capable of detecting contrasting portions of the targets 14 during daylight hours and a light source that is provided in target 18 during low light level conditions. For example, any suitable CCD array that is focused to provide an image of the targets 14 can be utilized, including video cameras, digital cameras, scanners, or other similar devices. Camera 12 should have a built-in auto iris and back light compensation function in order to obtain a good quality picture. Camera 12 may also be housed in a defrost heater having a fan to prevent frost or fog on the lens. Compressed air may also be provided to blow the lens of the camera in order to quickly dry fogs and water and also to protect the housing lens area from snowflakes and water drops. A light level detector 11 can also be used to detect overall light conditions. Use of this detector is more fully disclosed with respect to FIG. 16.

Targets 14 are disposed at various distances or ranges from the camera 12 which is located at a predetermined location, as shown in FIG. 1 (not to scale). For example, target 18 is located at a fairly close distance to the camera 12 to ensure that at least one target is visible during extremely low visibility conditions. Target 18, for example, may be located at a distance of approximately 25–40 meters from the predetermined location of the camera 12. This is so that at least one target can be detected in very low visibility conditions. Targets 20, 22, 24, and 26 are located at greater distances along the region in which the atmospheric visibility is to be measured. For example, target 20 is located at 100 meters, target 22 at 150 meters, target 24 at 200 meters, and target 26 at 300 meters. Of course, any desired distances can be used to locate the targets and these are only examples of locations of the targets 14 from the camera 12 that provide data that is useful in measuring atmospheric visibility. In highway applications, atmospheric visibility up to 300 meters may be important. Hence, the farthest target 26 is located at approximately 300 meters from the camera 12. Also, any desired number of targets can be utilized for determining visibility during daylight hours, as long as at least two targets are provided. Of course, more accurate measurements may be obtained by using more targets as will become apparent from the description below. For nighttime visibility, only one target is required. As shown in FIG. 1, target 18 is a lighted target that provides information for nighttime visibility, as explained below.

Referring again to FIG. 1, a computer 16 that has a frame grabber (video digitizer) that is used to capture an image of the targets and to process that image to generate an atmospheric visibility measurement. The frame grabber captures a single frame from the image that is generated by the camera 12. The image is in the form of a bit map in which each picture element (pixel) has a specified intensity. The intensity of the picture element is normally digitized into an 8-bit byte so that it can have one of 0 to 255 different levels. If 24-bit color data is provided in an RGB format, it can be converted to 8-bit black and white in accordance with equation 1:

$$M = 0.299 * R + 0.587 * G + 0.114 * B \qquad \text{Eq. (1)}$$

where M is the monochrome back and white data, R is the red component, G is the green component and B is the blue component. Equation 1 is a standard color to monochrome conversion formula.

Computer 16 of FIG. 1 can be a personal computer or any customized computing device, such as a micro-controller, or programmable logic device that is designed to perform the functions of the present invention. The frame grabber should use the same convention for capturing the image that is used by the camera 12. For example, if a video camera is used that provides an NTSC signal, the frame grabber should be able to capture images from the NTSC signal.

FIGS. 2–5 are a schematic illustration of a front view of targets 20–26 of one embodiment of the present invention. As seen from these figures, each of the targets increases in size as the range of the target increases from the camera 12. It is important that the camera 12 be able to view all of the targets 18–26 in a single image frame. The targets 20–26 are made so that they have an increasingly larger size as the distance at which they are deployed increases from the camera 12. As a rule of thumb, the size of the targets must be increased by a subtended angle of approximately 0.5 degrees with respect to the distance. In this manner, the resultant image of each of the targets is substantially the same size and can fit in the single frame of the camera 12.

As shown in FIG. 2, target 20 has a black background 30 with a white stripe 32 located in the center of the target running vertically. Similarly, FIG. 3 illustrates target 22 which has a black background 34 with a white stripe 36. FIG. 4 illustrates target 24 which has a black background 38 and a white stripe 40. FIG. 5 illustrates target 26 which has a black background 42 and a white stripe 44. The choice of black and white color in the targets are important, since this combination provides the highest contrast in monochrome black and white images. By providing these targets with increasing sizes so that a similar size image for each of the targets can be generated, a substantially equal amount of data can be obtained from the images of each of the targets. In this manner, a similar number of data points for contrast signals of each target can be generated for each of the targets since these targets appear to have substantially the same image size. This reduces error factors in obtaining contrast levels for each of the targets, as described below.

The targets illustrated in FIGS. 2–5 can also use a reverse contrast scheme. For example, each of the targets may utilize a white background with a black stripe. Further, a number of different stripes may be used with either contrast scheme, depending upon the number of contrast points desired, and the resolution of the camera 12. Of course, other shapes can be used, such as a black background with a white number identifying the target. The primary purpose, however, is to create contrasting edges in the image. White stripes against a black background creates the stronger contrast image and therefore provides the best edge information for measuring atmospheric visibility. Anything other than black and white can fail when the ground is covered with snow because white snow can create a strong edge or contrast at unknown distances, i.e., outside of the silhouette of the target. Additionally, if snow sticks to a target, a contrast edge can be generated between the white snow and the black background which can also serve as a contrast edge.

FIG. 6 is a front view of the night/day target 18. Target 18 has a panel 50 that has a white border 46 and a black background 48. An unfocused light source 51 is located in approximately the center of the target and is surrounded by the black background 48 when viewed from the front. The unfocused light source 51 provides a substantially spatially uniform source of light in the plane of the panel 51. In other words, the intensity of the light that is emitted from the target 18 in the plane of panel 50 is substantially equal. The black background 48 of panel 50 extends to the edges of the panel at 52 and 54. Sections 52 and 54 prevent the scattering of light from the unfocused light source 51 onto the white border portion 46 along the area that traverses sections 52 and 52 and passes through the unfocused light source 51. As is disclosed below, the atmospheric visibility at night is determined by detecting the amount of light scattering of the atmosphere along a horizontal line that passes through sections 52 and 54 and the unfocused light source 51. By blackening out the areas 52 and 54, reflections from particles back to the panel 50 does not cause unwanted light scattering in the regions 52, 54.

FIG. 7 is a side view of the night/day target illustrated in FIG. 6. As shown, the panel 50 is mounted so that panel 50 surrounds the light restrictor or light trap 56. The light restrictor (light trap) 56 is painted with a non-gloss black and is attached to the housing 58 to provide a light path 60 for light emanating from the night/day target 18. Housing 58 is a waterproof housing that houses the light source 62 and a diffusion lens 64. The light source 62 may comprise a simple light bulb that provides an output that is substantially uniform along the plane of the panel 50. Any non-uniformities in the light source 62 are substantially corrected by the diffusion lens 64 so that the light path 60 provides a substantially uniform intensity along the plane of the panel 50. A power line 66 is attached to the light source 62 to provide power to light source 62. As disclosed below, the power provided on power line 66 remains substantially constant so that the output of the light source 62 also remains substantially constant.

The light restrictor 56 illustrated in FIG. 7 defines the light path 60 so that a contrast edge is created between the light restrictor 56 and the panel 50 when viewed from the front, as illustrated in FIG. 6. The light restrictor 56 also protects the light source 62 and the diffusion lens 64 from snow and rain.

FIG. 8 is a schematic block diagram of a constant voltage power supply that is used to power a light bulb 62, that may comprise the light source of the day/night target 18 illustrated in FIG. 7. Referring again to FIG. 8, a constant voltage transformer 68 is plugged into a power source from a utility company. The utility company may provide a power source having 60 hertz AC with a voltage ranging from 95 to 130 volts. The constant voltage transformer 68 produces an output 70 that maintains a substantially constant voltage. This substantially constant voltage is applied to a variable transformer 72 which allows the user to change the voltage on power line 66 that is applied to light bulb 62. It is usually desirable to provide an output that ranges from approximately 0.7 to 2 foot candles in a light path 60 that has a diameter of approximately 8 inches. This allows the light source to provide the desired amount of light for detection by the camera 12. To provide proper measurements of visibility at night or under low light level conditions, it is important to produce a constant output from the light source along the light path 60 once the system has been calibrated. Hence, the constant voltage transformer 68 is important in providing a constant voltage to the light bulb 62 so that the light bulb 62 can provide a substantially constant output. Variable transformer 72 is useful when setting the output intensity (number of foot candles) of the light bulb 62. Also, the intensity of the light bulb 62 may decrease over time and it may be desirable to readjust the variable transformer 72 to provide the desired number of foot candle output of the light bulb 62. It may also be desirable to run the light bulb 62 at a lower voltage level. For example, the light bulb 62 may be run at 70 percent of the 117 volt RMS value of the AC signal which is approximately 74 volts RMS AC. This lengthens the life of the light bulb 62 and may provide a more uniform output of the light bulb along the spatial plane of the target panel 50.

FIG. 9 is a front view of the day/night target 18 with a calibration mask 74 mounted on the front of the target 18. As shown in FIG. 10, the calibration mask is mounted to the panel 50 of the target with mounting bolts 76. The calibration mask 74, as explained in more detail below may comprise a clear plastic material with light scattering material such as bubbles trapped inside and it is used to calibrate the system for measuring night visibility.

The operation of the system, under both day and night conditions, is described with reference to the flow diagrams of FIGS. 11 and 12. During the day, or under conditions other than very low light level conditions, the system operates in the matter illustrated in FIG. 11. As indicated at step 80 of FIG. 11, the camera 12 is mounted such that it generates an image that encompasses the area in which the targets 14 are disposed. At step 82, the image is captured using a frame grabber which generates a bit map of the image. At step 84, the computer then processes the bit map image to remove impulse noise using a media filter such as disclosed by R. C. Gonzales and R. E. Woods, *Digital Image Processing*, Addison-Wesley Publishing Company, Reading, Mass., 1993. Impulse noise tends to create false edges and could lead to a distortion of the computational results. The media filter processed image (or bit map) is referred to as the F-image, or the original image, for purposes of this description.

At step 86 of FIG. 11, the position of the first target is located using cross correlation techniques, such as those disclosed in *Digital Image Processing,* supra. Of course, any desired algorithm can be used to locate the first target. When visibility is low, targets that are located at distances that exceed the visibility cannot be detected in the bit map. Therefore, the target that is nearest to the camera is located first. The pixel data in the region where the target is expected to be located is processed first in accordance with the cross-correlation techniques since that expected position in the bit map has the highest probability of locating the target. However, winds can shift the camera 12 which will cause the targets to be located in different positions on the bit map. Hence, the cross-correlation techniques may be used in other locations on the bit map if the initial target is not located. Additionally, first target 18 has a different signature than the other targets so that the cross-correlation techniques can uniquely identify the target 18 from the other targets.

At step 88 of FIG. 11, the other targets are located by referencing the known positions of the other targets to the location of the first target and by cross-correlation techniques that are designed to ensure that each of the targets has been properly located. At step 90, the bit map is segmented so that only the pixels that represent the images of the targets are saved and the remaining portion of the bit map is discarded.

At step 92, an edge operator is applied to the segmented portions of the bit map to generate contrast signals E(j,k). The edge operator is described as follows:

$$E(j,k)=|X|+|Y| \qquad \text{eq. (2)}$$

where $$X=(p_2+2p_3+p_4)-(p_0+2p_7+p_6)$$

$$Y=(p_0+2p_1+p_2)-(p_6+2p_5+p_4)$$

and where the pixels surrounding the neighborhood of the pixel F(j,k) are numbered as follows:

| $p_0$ | $p_1$ | $p_2$ |
| --- | --- | --- |
| $p_7$ | $F(j,k)$ | $p_3$ |
| $p_6$ | $p_5$ | $p_4$ |

E(j,k) is the edge value obtained for the pixel location of F(j,k). The original Sobel operator is expressed as G(j,k)= $\sqrt{X^2+Y^2}$ and requires more computation time than the above described operator due to the square root and square computations.

At step 94, the computer 16 generates a representative contrast number $H_n$. $H_n$ is the average of a predetermined percentage of the highest contrast signals E(j,k) that are generated by the edge operator at step 92. In the representative contrast number $H_n$, the n is representative of the target number. For example, target 18 is target 1, target 20 is target 2, target 22 is target 3, target 24 is target 4, and target 26 is target 5. Hence, $H_1$ is the representative contrast number for target 18, while $H_2$ is the representative contrast number for target 20, etc. The representative contrast number can then be represented as follows:

$$H_n=\text{TopAvg}(E_n(j,k),c) \qquad \text{eq. (3)}$$

In the specific implementation of the present invention where there are five targets, i.e., n=1, 2, . . . 5, and the top 3 percent of the highest contrast signals are to be averaged for each of the targets, the following applies:

$$H_n = \text{TopAvg}(E_n(j,k), 3) \text{ for } n = 1, 2 \ldots 5 \qquad \text{eq. (4)}$$

$H_n$, in this case, essentially represents the average of the top 3 percent of the contrast values of each of the targets n. This averaging is performed to minimize the deviation by one or two pixels that are falsely recorded by the video camera 12 due to incorrectly calibrated charge couple devices or other sudden flashing effects in the image that are not caused by atmospheric visibility conditions. This averaging scheme operates as a robust protection mechanism for obtaining the highest contrast level signals from each target.

At step 96 of FIG. 11, the values of $H_n$ are plotted in a graph of contrast levels versus the distance x of each of the targets from the camera. In other words, a single value of $H_n$ is generated for each target and that contrast level value ($H_n$) is plotted against the distance x of that particular target from the camera. An example of an actual plot of data obtained is shown in FIG. 12. $H_n$ which is indicated as the maximum edge representation, is plotted against x, which is the distance of the target from the camera, which is shown as the computational visual range. As can be seen, data points are indicated for each of the targets which are located at 40 meters, 50 meters, 100 meters, 150 meters, 200 meters, and 300 meters. As can be seen from the plot of these data points, an exponential curve is generated as shown in FIG. 12.

Figure 12:
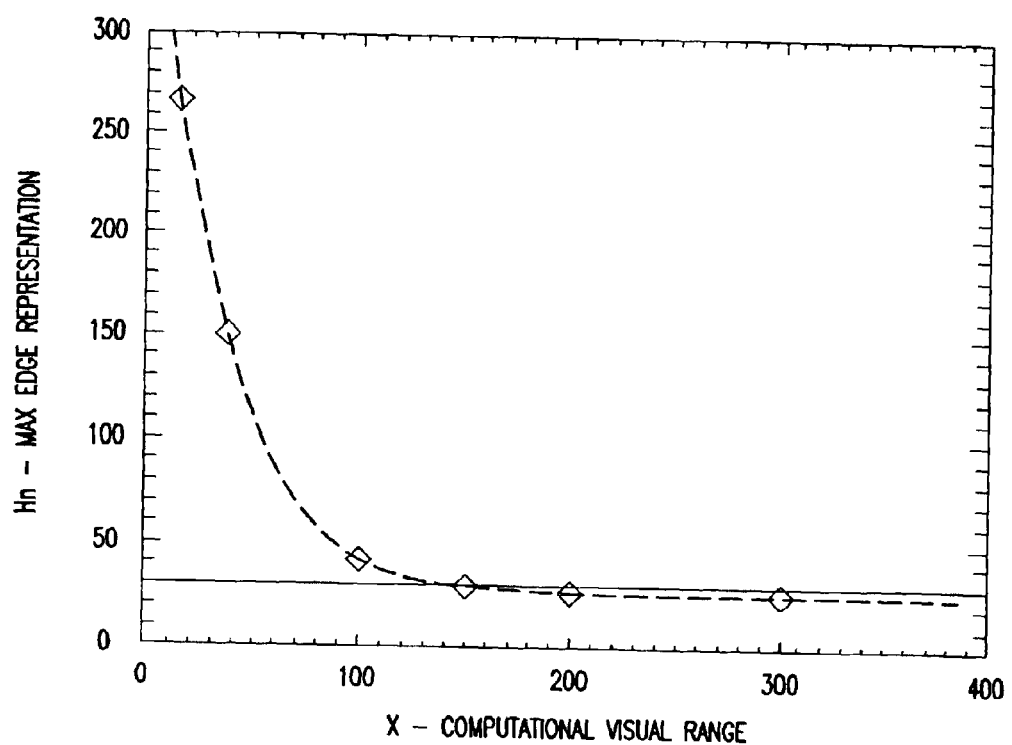
FIG. 12 is a graph of $H_n$ versus x.

At step 98 of FIG. 11, the computer 16 uses curve fitting techniques with the data points $H_n$ to generate the exponential curve illustrated in FIG. 12. In this manner, the constants $a_0$, $a_1$ and $a_2$ are determined for the exponential equation:

$$f(d) = a_0 e^{-a_1 d} + a_2 \qquad \text{eq. (5)}$$

where d is the distance of the target from the camera. The exponential curve illustrated in FIG. 12, is representative of the value of $H_n$ at any given distance d. A least squares fitting technique can be used to generate the exponential curve, such as disclosed by J. M. Ortega and W. G. Rheinboldt, *Iterative Solution of Non-Linear Equations and Several Variables*, Academic Press, Inc., San Diego, Calif., 1970. The curve f(d) illustrated in FIG. 12 represents the highest contrast levels, on average, versus the known distances of the targets from the camera.

Step 100 of FIG. 11 determines the atmospheric visibility. The atmospheric visibility is defined, in accordance with this embodiment of the present invention, as the distance where the edges of the contrasting portions of the target are degraded such that these edges are no longer distinguishable from the edges of the background noise. Referring to FIG. 12, the horizontal line that is drawn approximately represents the level of the contrasting edges that are no longer distinguishable from the background noise. This level of $H_n$ that is represented by the horizontal line is the threshold level of f(d), which is referred to as $f_{th}$. The visibility v can then be calculated as follows:

$$V = \frac{\ln[(f_{th} - a_2)/a_0]}{a_1} \qquad \text{eq. (6)}$$

As can be seen from FIG. 12, the threshold value of $H_n$ that is indicated by the horizontal line intersects the exponential curve at a distance x equal to 147 meters, which is the measured atmospheric visibility. This visibility can also be determined by detecting when the slope of the exponential curve reaches a predetermined minimum value, for example, a predetermined value of slope can be selected at which the exponential curve f(d), illustrated in FIG. 12, reaches a predetermined value. The value of x at that slope can then be determined which is the visibility measurement.

The advantages of generating atmospheric visibility measurements in accordance with this embodiment of the present invention are that the visibility measurements that are obtained in accordance with the present invention are based on recognition of visual features of targets, i.e., contrasting portions of the targets, and no special calibration is required for different types of atmospheric variations such as fog, rain, snow, smog, as is the case for scattered light measurements. Additionally, since the system uses an average of the highest contrast levels for each target, the results are not dependent on the target size, or the design, or shapes of the target, as long as valid contrast level signals can be obtained from each target. Hence, damages to the target or partial changes in the target do not significantly affect the outcome of the visibility measurements. Further, measurements made in accordance with this embodiment of present invention are not sensitive to variations resulting from the use of different types of cameras, zoom factors, camera resolution or other camera properties. Thus, camera replacement does not require recalibration of the computational method. Also, since the system generates a visibility measurement based on visual features, visibility measurements directly measure the visibility in accordance with the definition of visibility set forth above.

Measuring Visibility in Low-light Conditions

Figure 13:
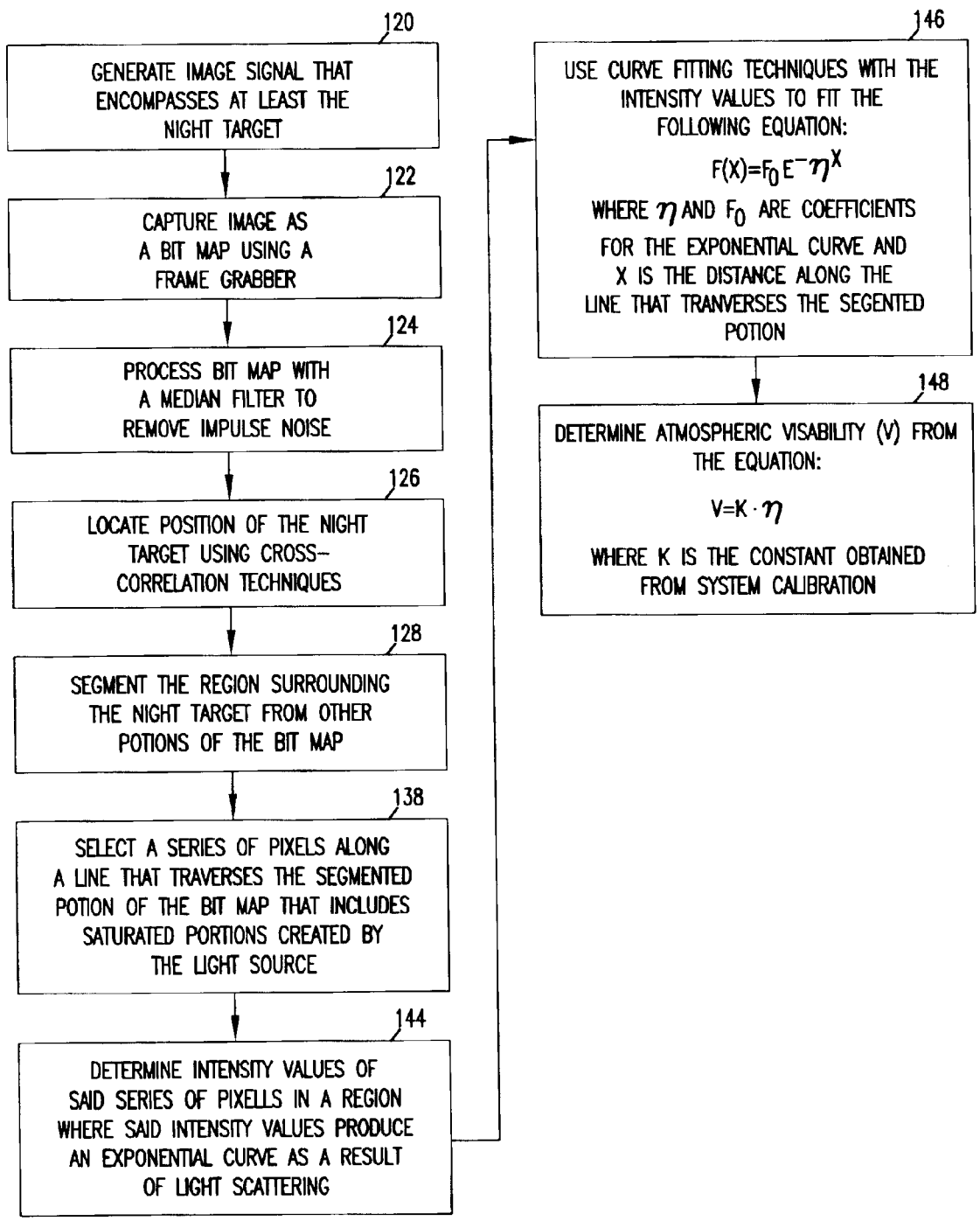
FIG. 13 is a flow diagram of the steps performed to measure atmospheric visibility in low light level conditions.

FIG. 13 is a flow diagram that illustrates the manner of detecting atmospheric visibility during low light level or nighttime conditions. Since most video cameras cannot see the targets or the contrasting portions of the targets at night, the present invention utilizes a light source mounted in a target to measure nighttime visibility. The night target illustrated in FIGS. 6 and 7 is utilized for the steps that are performed in FIG. 13 to detect nighttime visibility. At step 120 of FIG. 13, an image signal is generated by the video camera 12 that encompasses an area surrounding the night target. This image is then captured as a bit map using a frame grabber at step 122. At step 124, the computer 16 processes the bit map with a median filter, in the manner disclosed above, to remove impulse noise. The position of the night target is then located using a cross-correlation technique at step 126. At step 128, the region surrounding the night target is segmented from other portions of the bit map. A large enough region is segmented from the bit map to include the diffusion effect of the light source that is caused by the atmosphere.

Atmosphere visibility at night is closely related to the amount of scattered volume of the image from the saturated region of the light source. Saturated regions of the light source are identified as areas that are completely white and are physically located on the image in the central region of the light path of the light source.

Figure 14:
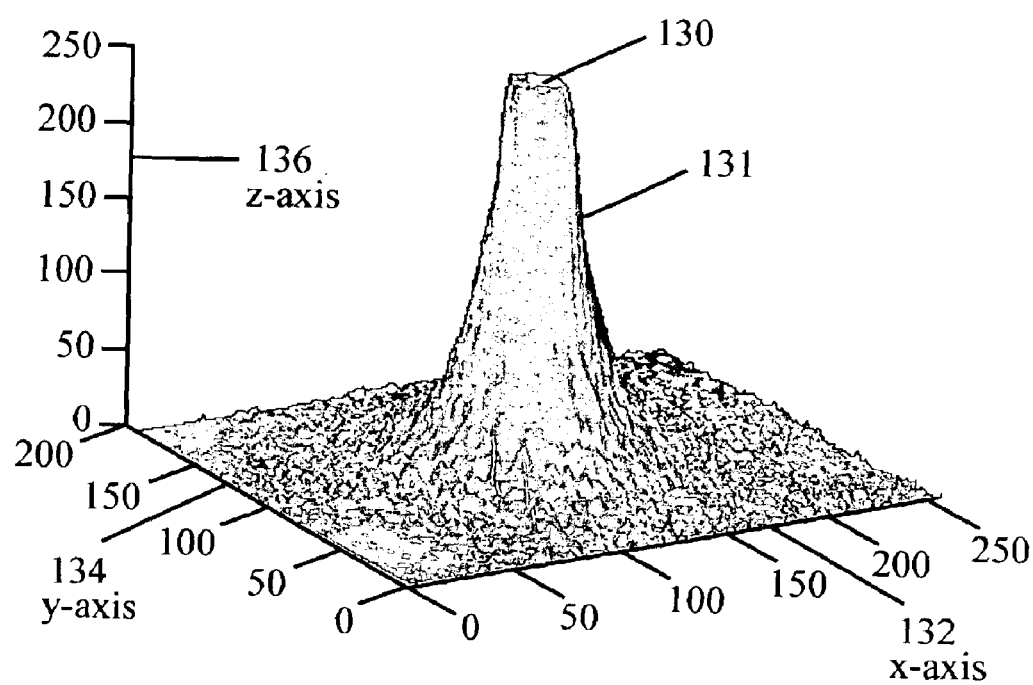
FIG. 14 is a three dimensional graph of light intensity values of the night target.

FIG. 14 is a three-dimensional plot of the detected light intensity of a bit map image in the segmented target region. The three-dimensional plot illustrated in FIG. 14 shows the scattered volume in the X axis 132 and Y axis 134 of the light intensity levels that are plotted in the Z axis 136. As can be seen from FIG. 14, the saturated regions are shown at 130. The volume of the cone shape is directly related to the atmospheric visibility. As the volume increases, the visibility decreases. The characteristics of the cone shape illustrated in FIG. 14 are that the slope of the cone follows an exponential decay relation.

Figure 15:
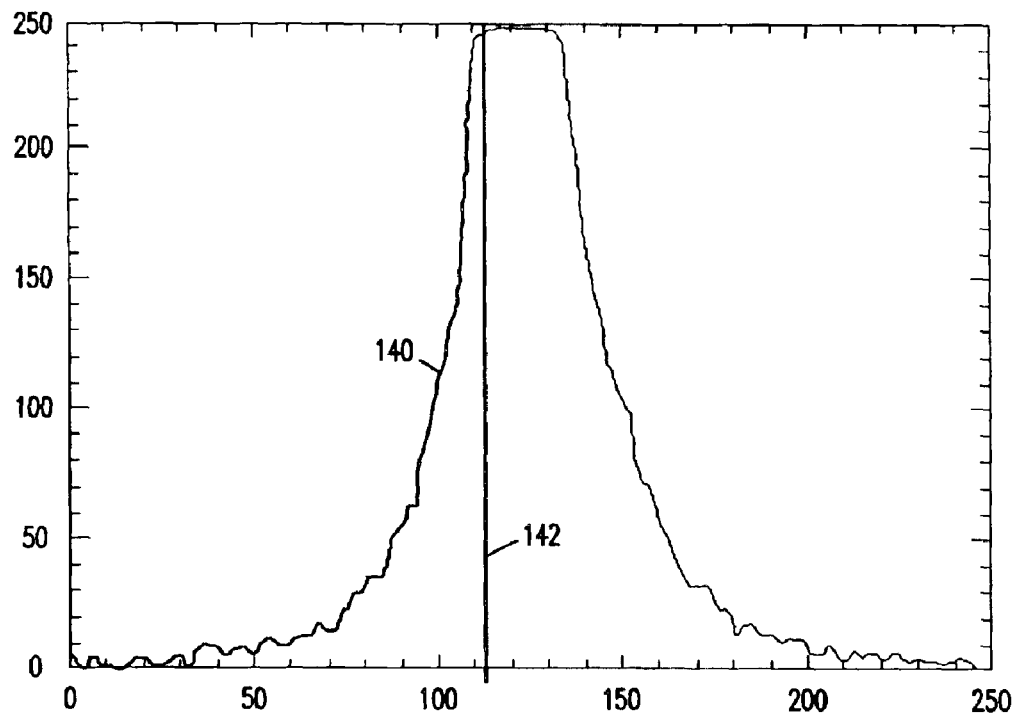
FIG. 15 is a two dimensional graph of light intensities that are taken from the three dimensional graph of FIG. 14.

FIG. 15 illustrates a plot of the intensity of the pixels that correspond to a cross-section along the X axis through the center of the cone 131 illustrated in FIG. 14. Referring to FIG. 13, at step 138 a series of pixels along a line that traverses a segmented portion of the bit map that includes the saturated portions is created by the light source. This corresponds to the plot of pixel intensities illustrated in FIG. 15. As shown in FIG. 15, an exponential curve 140 that represents the light intensity values of the scattered signal, is created by insertion of the ordinate line 142.

Referring to FIG. 13, at step 144, intensity values of the series of pixels corresponding to exponential curve 140 (FIG. 15) are determined in a region where the intensity values produce an exponential curve as a result of the light scattering. At step 146 of FIG. 13, curve fitting techniques are used with the intensity values illustrated in FIG. 15 of curve 140 to fit the following equation:

$$F(x)=F_o e^{-\eta x} \qquad \text{eq. (7)}$$

where $\eta$ and $F_o$ are coefficients for the exponential curve 140 and x is the pixel location from the left side of the plot illustrated in FIG. 15. As the area under the curve 140 becomes larger, the visibility becomes lower and the exponential curve becomes flatter. In general, it is determined from equation 7 that visibility is proportional to the coefficient $\eta$. In other words, the following relationship holds:

$$V \propto \eta \qquad \text{eq. (8)}$$

From equation 8, it can be deduced that the following is true:

$$V = k \cdot \eta \qquad \text{eq. (9)}$$

where k is a constant scaling factor that can be determined by calibrating the night vision device of the present system and V is the measured visibility at night. Referring to FIG. 13, the computer 16 determines the value for the constant k by using calibration factors. The constant k is dependent upon the intensity of the light source and properties of the video camera 12 such as resolution. Therefore, the coefficient $\eta$ must be known to compute the visibility in accordance with equation 9.

One way of determining the constant k is using a SLM. Since SLMs are relatively accurate under fog, the SLM can be used as a reference to estimate the constant k. In accordance with this process, the visibility is first measured using a SLM under foggy conditions which would give the value V. Then, using the processes disclosed above, the value of constant $\eta$ can be determined. Since the values of V and $\eta$ are known, k can be computed using equation 9.

However, since SLMs are generally expensive and the visibility cannot be measured until the value of the constant k is found on a foggy night, other solutions may be more advantageous. For example, a standard calibration mask, such as illustrated in FIGS. 9–10, can be used to generate a known amount of light scattering. A mask such as mask 74 of FIG. 9 can be designed to provide a predetermined visibility such as a visibility of 140 meters. To calibrate the night vision system, the mask is placed in the light path of the day/night target 18 as illustrated in FIGS. 9 and 10. In total darkness on a clear night, an image of the light source can be captured and the process described above can be carried out to obtain a value for the constant $\eta$. In this case, since both $\eta$ and V (140 meters) are known, k can be calculated from equation 9 to calibrate the system.

A close review of equation 7 raises some interesting questions. Equation 7 can be rewritten as follows:

$$F(x)/F_o = e^{-\eta x} \qquad \text{eq. (10)}$$

This looks very similar to the equation that describes the contrast ration of a black object in accordance with the exponential decay law described by S. Q. Dauntley, "The Reduction of Apparent Contrast by the Atmosphere," *J. Opt. Soc. Am.*, vol. 38, 179–191. As disclosed by *Dauntley, infra:*

$$C/C_o = e^{-\sigma d} \qquad \text{eq. (11)}$$

Where $C_o$ is the inherent contrast against the sky, that is, the contrast measured at the target, C is the apparent contrast of the target observed at a distance d, and $\sigma$ is the atmospheric attenuation coefficient (extinction coefficient). A comparison of equations 10 and 11 allows one to deduce that contrast exists at night and that the light source of target 18 allows the system to measure contrast. The existence of contrast at night and the ability to measure that contrast has not been known in the prior art.

Selecting a Visibility System

Figure 16:
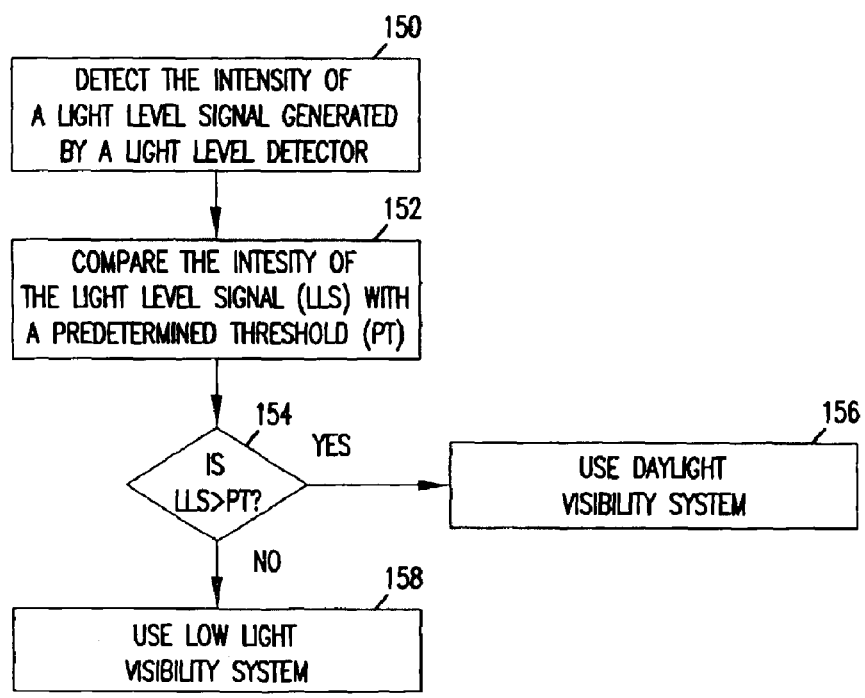
FIG. 16 is a flow diagram illustrating one method of selecting an atmospheric visibility measurement system.

Since the present target-based system may use two or more different methods for determining visibility, i.e., one method for determining daytime visibility and another method for determining visibility at night, an automated way of determining which method to use is advantageous. One method can employ a light sensor to determine the amount of light and thereby switch the system for determining whether to use the visibility measurement system for daylight hours or the visibility measurement system for night. FIG. 16 is a flow chart that discloses the steps of this method. At step 150 the intensity of a light level signal generated by a light detector such as light level detector 11 of FIG. 1 is detected by the system. The intensity of the light level signal is then compared with the predetermined threshold at step 152. At step 154 a decision is made as to whether the light level signal is greater than the predetermined threshold. If it is, the daylight visibility system is used as step 156. If it is not, the low light visibility system is utilized as step 158 to measure atmospheric visibility. However, this approach requires an additional light sensor and it adds additional cost and complexity to the system.

Figure 17:
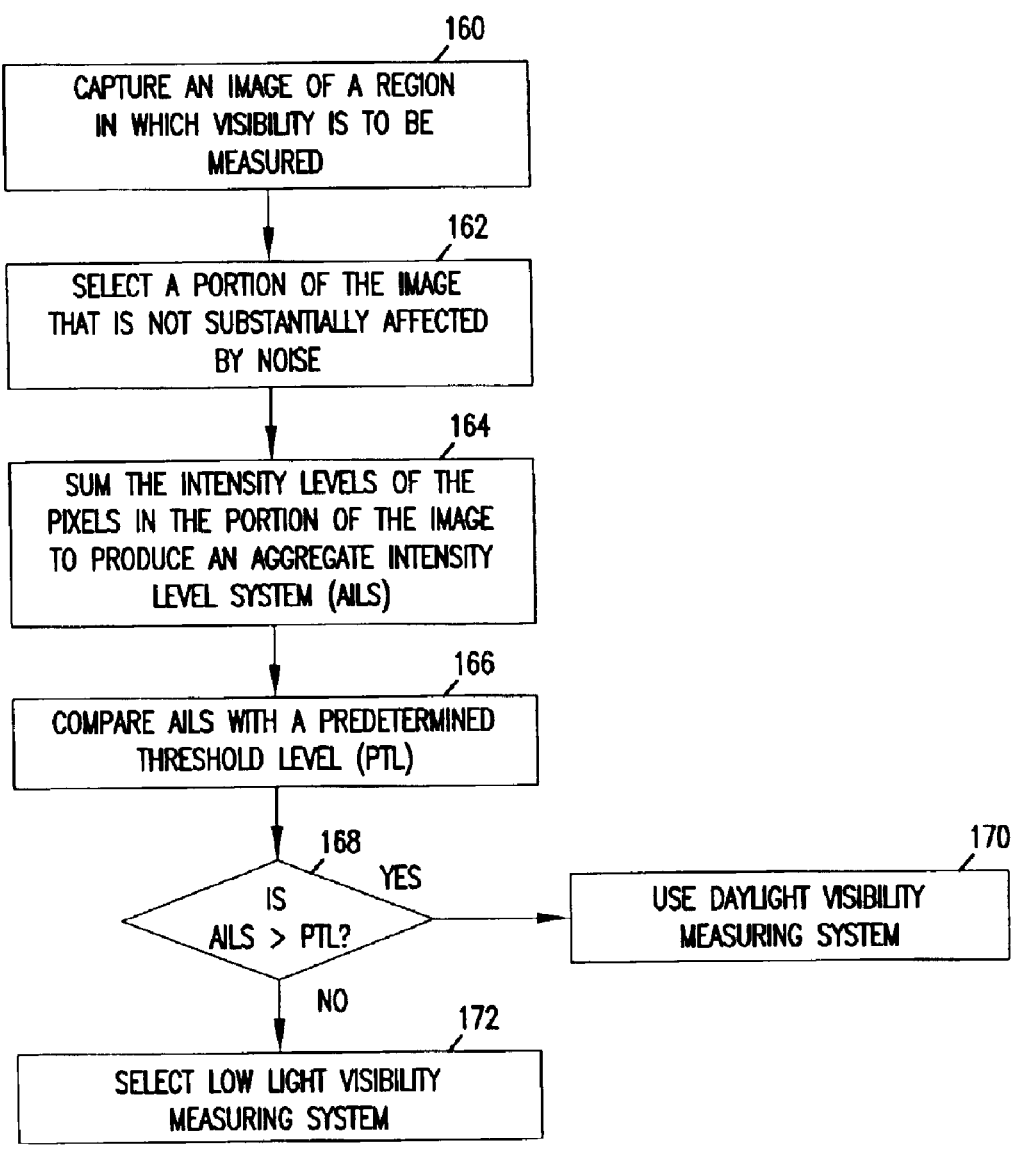
FIG. 17 is a flow diagram illustrating another method of selecting an atmospheric visibility measurement system.

Another method of automatically selecting the detection system is to generate a sum signal of the light intensity of a portion of the captured image, such as an area where trees or vegetation is present and other interfering factors are not present, such as car headlights, etc. A threshold value can then be generated based on the light intensity signal and the day or night method can be selected accordingly. FIG. 17 is a flow diagram illustrating the steps of selecting a visibility system in accordance with this method. At step 160, an image of a region which visibility is to be measured is captured by the camera 12. A portion of the image that is not substantially affected by noise is then segmented from the rest of the image at step 162. At step 164, the intensity levels of the pixels in the segmented portion of the image are added together to produce an aggregate intensity level signal. At step 166, the aggregate intensity level signal is compared with a predetermined threshold level. At step 168, a decision is made as to whether the aggregate intensity level signal is greater than the predetermined threshold level. If it is, the daylight visibility measurement system is selected at step 170. If it is not, the low light visibility measurement system is selected at step 172.

Figure 18:
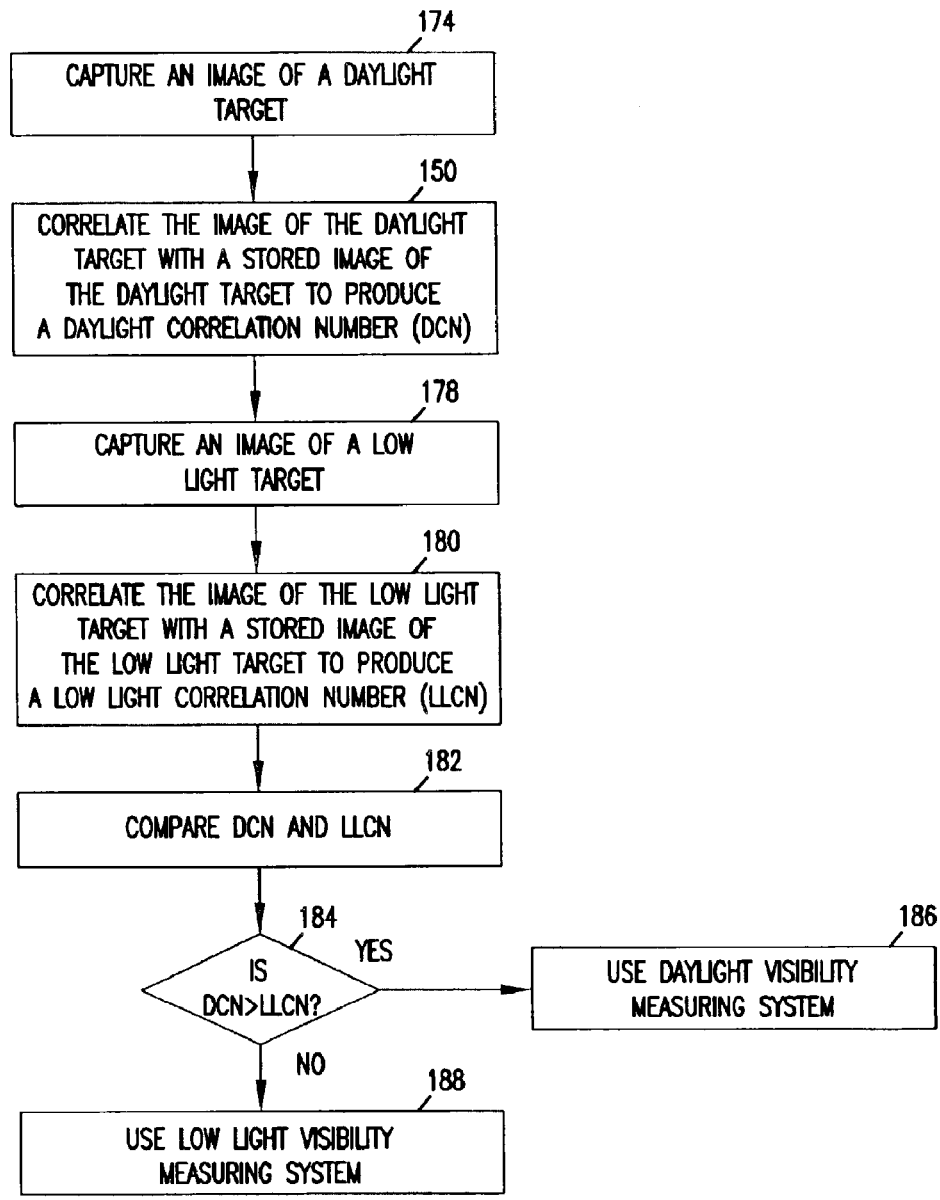
FIG. 18 is a flow diagram illustrating still another method of selecting an atmospheric visibility measurement system.

A third alternative method using correlation can be employed. According to this method, the targets are initially located in the manner described above. Then, a correlation process is performed for the day targets using a stored pattern. A similar correlation is then performed for the night target. A decision is then based on the more strongly correlated result. FIG. 18 is a flow diagram illustrating the steps for carrying out this method of selecting an atmospheric visibility measurement system. At step 174, an image of a daylight target is captured by the camera 12 and the frame grabber. At step 176, this image of the daylight target is then correlated with a stored image of the daylight target to produce a daylight correlation number. At step 178, an image is captured of the low light target. At step 180, the image of the low light target is correlated with the stored image of the low light target to produce a low light correlation number. At step 182, the daylight correlation number is compared to the low level correlation number. At step 184, the decision is made as to whether the daylight correlation number is greater than the low light correlation number. If it is, a daylight visibility measurement system is used at step 186. If it is not, a low light visibility measurement system is used at step 188.

The system therefore provides unique methods of determining visibility during both daylight and nighttime hours. Since the video camera records a visual image of the region in which atmospheric visibility is to be measured, that image includes all of the atmospheric effects that may affect visibility. In this manner, the video image not only represents the light scattering effect, but also includes all of the atmospheric conditions that may influence visibility. Additionally, video cameras display a field of view along the line of sight instead of a small region adjacent a SLM. Thus, the images represent a much larger area than that which is detected by SLMs. Therefore, the visibility computed using the video image based approach is much less prone to local variations and atmospheric conditions. Further, the visibility measurements made in accordance with the daytime targets are based on the contrast levels that are detected for the targets. The visibility translation errors due to significant scattered light properties for different types of atmospheric particles are much smaller for the present invention than that of SLMs. Hence, the present invention does not require special calibration for atmospheric visibility that is affected by snow or rain, as is the case for SLMs.

Measurement of Relative Visibility

In a preferred embodiment, visibility may be measured without the use of specialized targets by processing images to determine relative visibility. For the purpose of description, the system may be referred to as "targetless." The system does in fact utilize "targets" in the sense that it perceives objects in the view of the camera, but it does not depend upon the placement of specialized targets having predetermined visual characteristics or locations. Targets such as those shown in the figures may be used of course, but their presence is not required.

Figure 27:
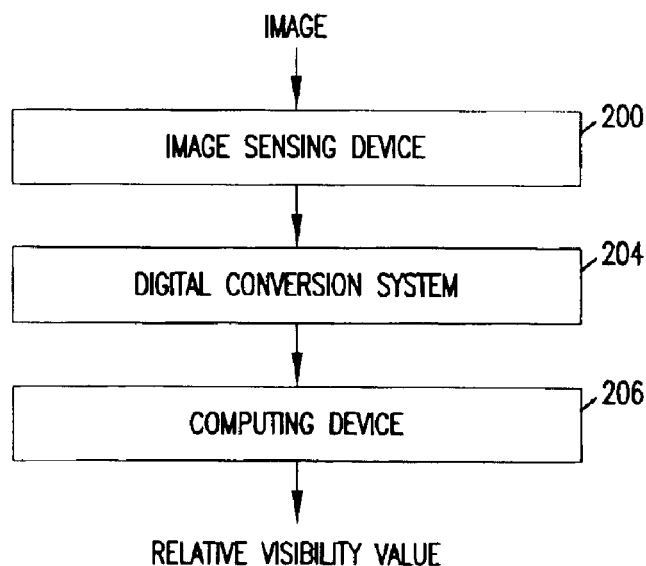
FIG. 27 is a schematic illustration of a system for receiving data and computing a relative visibility value.

In one embodiment, illustrated schematically in FIG. 27, a "targetless" visibility measurement system includes an image sensing device 200, such as a video camera, a digital conversion system 202 that maps the view of environment into two-dimensional data array, and a computing device 204 that converts the digital data to a value that represents visibility. The camera is preferably fixed in a stationary location, such as a pole, and pointed such that objects with varying distances from the camera are visible. Preferably, the camera is positioned so that the horizon is visible, so that objects at both near and far distances are visible from the camera.

Computation of relative visibility involves a parameter called a "Visibility Index" (VI), which is a summation of measurable visual characteristics in the image that influence the visibility. The details on how to compute VI will be presented later. Let VI measured at location l at time t be denoted as VI(l,t). Suppose that VI was taken under an ideal visual condition, i.e., a clear day with no cloud cover. Let this VI be denoted as $VI_{opt}(l)$, then it should satisfy:

$$VI_{opt}(l) = \underset{t}{\text{Max}} VI(l, t) \quad \text{(Eq. 12)}$$

If the location was fixed, it can be written without l. The Relative Visibility (RV) is then defined as:

$$RV(l, t) = 1 - \frac{VI_{opt}(l) - VI(l, t)}{VI_{opt}(l)} = \frac{VI(l, t)}{VI_{opt}(l)} \quad \text{(Eq. 13)}$$

Notice that the range of RV is between 0 and 1; the maximum occurs when $VI_{opt}(l)=VI(l,t)$; the minimum occurs when VI(l,t)=0. RV essentially represents a parameter in which how close the measuring video image is to the image taken under an ideal condition in terms of the image features extracted by VI.

Ideally, VI should be a linear function of atmospheric visibility. However, in order to be able to measure atmospheric visibility from video images, the distance of the objects or pixels in the image must be known. Unfortunately, such distance information is lost from the 2-D video imaging process and cannot be recovered from the image alone, unless specific distance from a known object to camera and the inherent contrast of the object are known.

This information deficiency can be addressed by computing relative visibility. Object distance information is not required to compute the relative reduction of visual conditions in relation to the ideal condition. The computation can be accomplished using the influential factors such as reduction of edge information and contrast trends in the area that has a property of uniform distance change.

Figure 25:
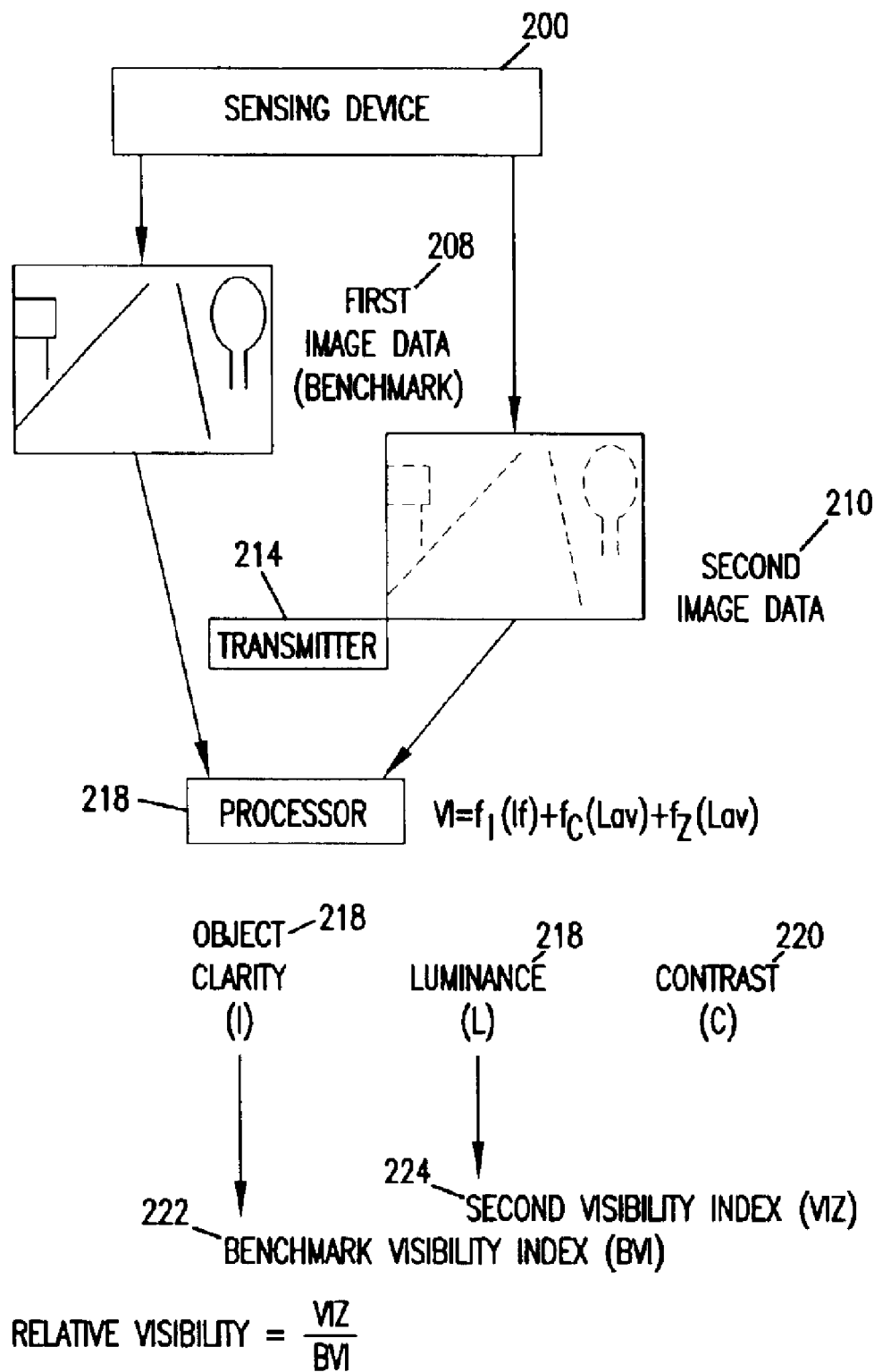
FIG. 25 is a schematic illustration of one embodiment of a system for determining relative visibility.

Referring now to FIG. 25, a sensing device 200 such as a video camera senses an environment. A first set of image data 208 obtained under a benchmark condition is output from the camera. The benchmark condition should be reasonably close to an optimal or "ideal" visbility condition—i.e. a clear day. A second set of image data 210 is output from the camera under a different environmental condition. A transmitter 212 may be used to send the data to a different location. Alternatively, the data may be processed locally and the result may be transmitted. The data is received by a processor 214. The processor 214 computes a visbility index (VI) for each set of data based upon factors that affect visibility, as described more fully in paragraphs below. In a preferred embodiment, the processor accounts for object clarity (I) 216, luminance (L) 218 and contrast (C) 220. The processor may also estimate the distance to objects in the images.

Referring again to FIG. 25, the processor computes a benchmark visibility index 222 for the bencmark condition from the benchmark data 208 and a second visibility index 224 for the second condition from the second set of data 210. Relative visibility is computed as the ratio of the second visibility index to the benchmark visibility index.

Figure 26:
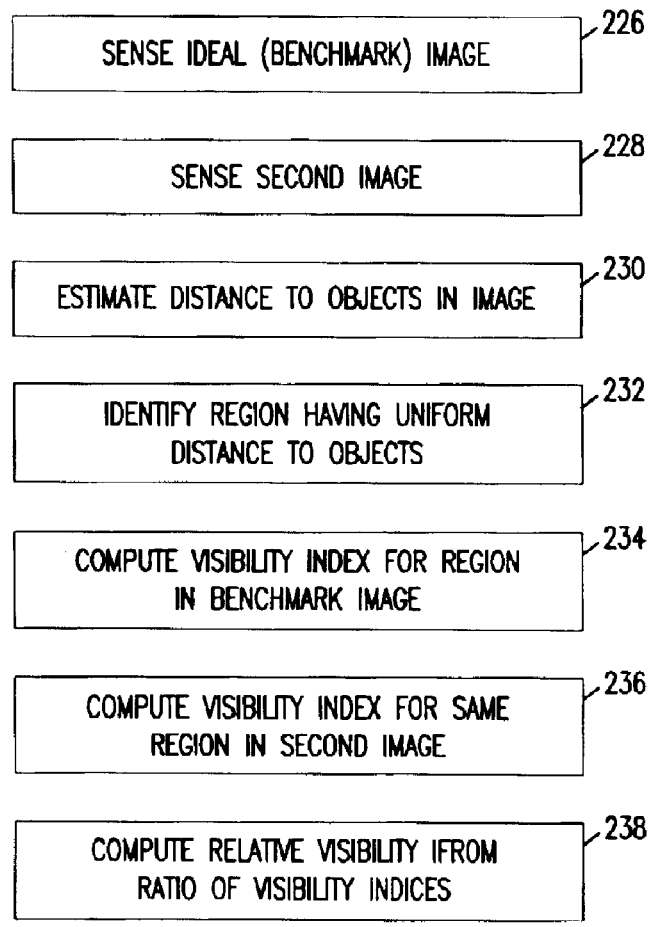
FIG. 26 is a diagram of steps for computing relative visibility.

Referring to FIG. 26, a diagram showing steps for one embodiment are provided. First, in step 226, a system senses an "ideal" or "benchmark" image for use as a basis for determining relative visibility. In step 228, a second image is sensed. In optional step 230, the distance to objects in one or both of the images is estimated. In optional step 232, regions having uniform distance from the camera are identified. For example, as further described below, an image of a highway may include static objects (i.e. a road sign or building) along the roadway, from which relative visibility may be determined, along with dynamic objects, such as vehicles, which may not provide a good basis for computing relative visibility because their position as well as inherent contrast (i.e. color) varies substantially from image to image. Depending on the environment, stop 232 may be omitted in some applications, such as when the environment is essentially constant.

In step 234, a visibility index is computed for the first image. In some embodiments, the entire image may be used for the computation, while in other embodiments only a designated portion having static objects may be used. In step 236, a visibility index is computed for the second image. In step 238, a relative visibility value is computed as the ration of the visibility indices. The steps in FIG. 26 do not all necessarily need to occur in the order shown. For example, if step 232 is omitted, step 228 could occur after step 234.

Returning now to the method for analyzing data to provide a relative visibility value, extraction of features that affect atmospheric visual range from images begins with consideration of the fundamental principle of visual range in atmosphere. One of the most fundamental principles governing visual range is expressed using luminance of a black target against horizon sky as:

$$L_b = L_b^0 e^{-\sigma x} + L_h(1 - e^{-\sigma x}) \quad \text{(Eq. 14)}$$

where $L_b^0$ is the inherent luminance of a black target that is non-zero; $L_b$ is the apparent luminance of the target; $L_h$ is the luminance of horizon sky; $\sigma$ is the extinction coefficient (inverse of distance function); and x denotes the distance from the target to the observation point. The first term describes exponential decay of inherent luminance of the target as a function of distance and atmospheric condition, and the second term describes the air light changes.

Assume that an object A has background B. Writing luminance equations Eq.3 for A and B and finding the difference gives:

$$L_A - L_B = (L_A^0 - L_B^0)e^{-\sigma x} \quad \text{(Eq. 15)}$$

where $L_A$ and $L_B$ are the apparent luminances of A and B, and $L_A^0$ and $L_B^0$ are the inherent luminaces of A and B, respectively. Using a difference notation, Eq. 15 can be written as:

$$D_{AB} = D_{AB}^0 e^{-\sigma x}. \quad \text{(Eq. 16)}$$

The difference $D_{AB}$ essentially represents a contrast formed by foreground A and background B in an image. If visual range V from the camera is determined at a threshold $\epsilon = D_{AB}/D_{AB}^0$, which would be the point where the difference between foreground and background is no longer distinguishable, then the visual-range is computed from Eq. 16 by replacing x with V as:

$$V = -\frac{\ln \varepsilon}{\sigma}. \quad \text{(Eq. 17)}$$

This principle given in Eq. 17 has been the basis for almost all of visibility studies and instruments developed. See W. E. Knowles Middleton, *Vision Through Atmosphere*, University of Toronto Press, 1968. It should be noted that $\epsilon$ is always less than 1 since $D_{AB} \leq D_{AB}^0$, resulting in a positive visual range. This relation obtained for the standard definition of contrast is referred to as the Koschmieder's rule [2,3], that is, if contrast is defined as:

$$C_{AB} = \frac{L_A - L_B}{L_B}. \quad \text{(Eq. 18)}$$

This normalization is not necessary in video images, since pixel values are already normalized into a digitizing resolution, when the image of real-world scene is converted into a digital form.

For simplicity, let $C_x$ denote the apparent contrast of an object and $C_x^0$ the inherent contrast at distance x. Then Eq. 16 under a uniform extinction coefficient can be written as:

$$C_x = C_x^0 e^{-\sigma x} \quad \text{(Eq. 19)}$$

This relation was first derived by Duntley, which enabled visual-range measurement from any background using the contrast reduction. National Weather Service, *Federal Meteorological Handbook No.1*, December 1995.

Next, consider a line of sight from the camera that linearly increases the distance, and integrate the contrasts along the selected line from zero to infinity, i.e., $$\int_0^\infty C_x dx = \int_0^\infty C_x^0 e^{-\sigma x} dx = \frac{C_x^0}{\sigma} \quad \text{(Eq. 20)}$$

It is assumed that the inherent luminance $C_x^0$ is a constant, which would be equivalent to placing objects with the same contrast along the line that linearly increases the distances from the observation point. Since inverse of extinction coefficient is proportional to visual range as shown from Eq. 17, the following relation holds:

$$\int_0^\infty C_x dx \propto V \quad \text{(Eq. 21)}$$

From Eq. (9) and (10), it is apparent that atmospheric visibility is strongly correlated (linear) to integration of contrasts, if objects with the same contrast can be placed in a straight line. However, such a set up can only be possible in theory.

In order to further examine the visual-range principle, consider that images are taken at the same location under different visual range conditions. Let two extinction coefficients be $\sigma_1$ and $\sigma_2$, and the corresponding observed contrasts be $C_{x,1}$ and $C_{x,2}$, respectively; then the following relations holds, $$\frac{1}{\sigma_1} = x \ln \frac{C_{x,1}}{C_x^0} = V_1 \quad \text{(Eq. 22)}$$

and $$\frac{1}{\sigma_2} = x \ln \frac{C_{x,2}}{C_x^0} = V_2 \quad \text{(Eq. 23)}$$

where $V_1$ and $V_2$ denote the corresponding visual ranges and $C_x^0$ is the inherent contrast at distance x. Suppose that two conditions are compared by simple subtraction, that is, $$V_1 - V_2 = x(\ln C_{x,2} - \ln C_{x,1}) \quad \text{(Eq. 24)}$$

Note from Eq. 24 that, when two images are compared, inherent contrasts are no longer a factor, but distance information is needed. More specifically, when two identical locations are compared, distance and the contrasts are the only parameters needed for comparison of two different visibility conditions. If two images are taken from the same location, inherent contrasts should be considered identical. Therefore, a good measurement that is a direct function of visibility is given by, $$V_x = x \ln C_x \quad \text{(Eq. 25)}$$

However, if the distances of objects from camera are unknown, Eq. 25 cannot be directly computed. As a solution, a distance model based on terrain shapes can be estimated and applied, which will be presented later. Another problem is that the resolution of $C_x$ is limited by the pixel resolution, which leads to less accurate measurements.

For a more effective computation that is less critical to pixel resolution, a formulation based on threshold is introduced. Based on the definition of visual range show in Eq. 17, let the threshold be $\theta_x = \ln C_x / C_x^0$, where the object and background are no longer distinguishable, which means visibility at x can be directly computed by $$V_x = x \ln \theta_x \quad \text{(Eq. 26)}$$

Notice that if $\ln \theta_x = 1$, then x would be the visual range, which follows the basic definition of visibility. To extract this threshold information from an image, an indicator function $I_x$ is defined as $$I_x = \begin{cases} 1 & \text{if } C_x \geq C_\theta \\ 0 & \text{if } C_x < C_\theta \end{cases} \quad \text{(Eq. 27)}$$

where $C_\theta$ is the threshold in which inherent contrasts of all objects in the image are greater than this value. It is now clear that $$V \propto I_f = \sum_x x I_x \quad \text{(Eq. 28)}$$

Since $I_x$ is directly computable from the images using Eq. 27, Eq. 28 is computable if the distances in the image are estimated. An example terrain model that allows computation of distance will be described later.

Eq. 28 could provide reasonably accurate visibility computation, but due to noise characteristics in the camera especially in CCD, relying on the contrast alone is prone to error by false edges. There are other factors that influence visual range in an image that can improve. Because visual range is reduced more by light scatter than absorption, when visual range is reduced, the average of the luminance approaches towards luminance of horizon sky. In fact, under foggy condition, the following relation holds, $$V \propto L_{max} - L_{av} \quad \text{(Eq. 29)}$$

where $L_{max}$ is the maximum luminance that corresponds to horizon sky and $L_{av}$ is the average luminance of the image. As long as the images are taken at the same location under the same arrangement of objects, Eq. 29 is a good estimate of visibility.

For human perception of visibility, object recognition condition is another important factor. In image processing, such information can be estimated through the existence of edge information. In a simple model, this information can be estimated through average contrast or variance of luminances.

In summary, we propose computation of VI using the three factors mentioned in order to capture features of an image that provides relation visual range and visual information assessment, i.e., $$VI = f_1(I_f) + f_2(L_{av}) + f_3(C_{av}) \quad \text{(Eq. 30)}$$

where $f_i$ are control functions for each component and $C_{av}$ is the average of the contrast. The contrast average, $C_{av}$, may be replaced with a variance of the image depending on whichever computation is efficient. Eq 19 essentially tells that VI is a function of clarity of the objects, the average luminance, and the average contrast of the image.

Figure 19:
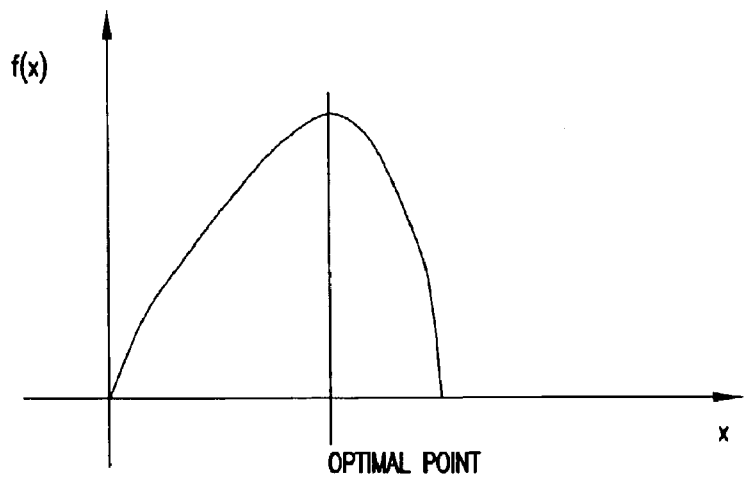
FIG. 19 is a graph showing a range controlled parabolic function that represents the relationship between contrast and visibility.

For the choice of control functions, a sensible choice of a function should be based on the characteristics of human perception of images. For example, visibility increases as the average luminance decreases in the image. However, this rule only applies up to a certain threshold. If the average luminance decreases beyond this threshold, visual range is rather decreased. A similar effect occurs for the average contrast. Visual range increases only up to a certain threshold level of contrast. If the average contrast reaches beyond this threshold, visual range begins to decrease again. For example, a very high contrast actually reduces visibility by overexciting the eye. In essence, this characteristic follows an Entropy type of information function, where there always exists an optimal level. This threshold effect can be estimated through a range controlled parabolic functions as shown in FIG. 19.

For further details on this function, example parabolic functions used to verify the measurements are shown. These control functions were derived after inspecting the actual images and by inspecting ideal conditions. Note also that these parabolic functions serve as weighting factors for each component of visibility index.

Control function for indicator function:

$$f_1(I_f) = \begin{cases} -(I_f - 10{,}000)^2/333{,}333 + 300, & \text{if } I_f \leq 10{,}000 \\ -(I_f - 10{,}000)^2/1{,}000{,}000 + 300, & \text{if } I_f > 10{,}000 \end{cases}$$

Control function for average luminance:

$$f_2(L_{av}) = \begin{cases} -(L_{av} - 160)^2/85 + 300, & \text{if } L_{av} \leq 160 \\ -(L_{av} - 160)^2/176 + 300, & \text{if } L_{av} > 160 \end{cases}$$

Control function for average contrast $$f_3(C_{av}) = \begin{cases} -(C_{av} - 42)^2/20 + 300, & \text{if } C_{av} \leq 42 \\ -(C_{av} - 42)^2/6 + 300, & \text{if } C_{av} > 42 \end{cases}$$

Figure 20:
FIG. 20 shows an image with a relative visibility (RV) of 0.36.
Figure 21:
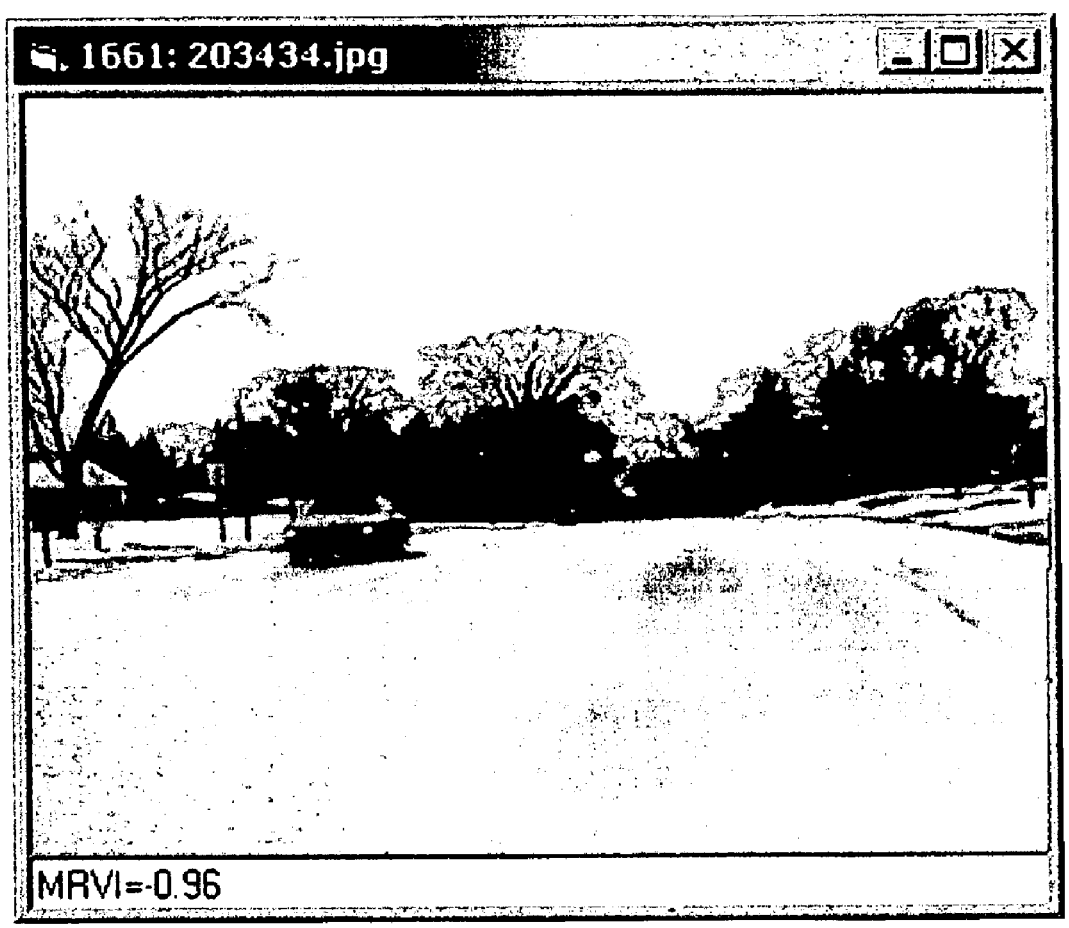
FIG. 21 shows an image with relative visibility (RV) of 0.96.

After computation of VI, RV is computed using Eq. 20, which then can be translated into visibility, i.e., $$V = e^{aRV} \quad \text{(Eq. 31)}$$

where $\alpha$ would be a constant that will vary depending on the characteristics of camera and the objects available on the image. For further illustration, two images taken while driving trucks are shown. FIG. 20 was taken under about 600 meters of visibility and the computed RV was 0.36. Notice that road boundaries are not visible. Although a different location, another picture is shown in FIG. 21, which was taken during a clear day. Its RV comes out to be 0.96. These numbers indicate that FIG. 20 has about 36% of visual information, and FIG. 21 has about 96% of information in reference to an ideal clear day, respectively. The ideal condition was theoretically defined through the example equations shown above, which is located at the peak of the curve.

Contrast Computation from RGB Color Image

There are some important issues in computation of contrast from color images. Color images are frequently recorded using RGB color space, which is represented by red, green, and blue primaries as orthogonal axis. Although contrasts may be computed using luminance conversion from the RGB color space, it looses information on color contrast that human perceives. For example, yellow lane marks in the pavement does not show as significant contrast when the color distance is measured from the RGB space, but human perceives them as a high contrast. Indeed, RGB color primaries were developed for color reproduction of monitors, in that some portions of colors do not scale like human color perception. Roy Hall, *Illumination and Color in Computer Generated Images,* Springer-Verlag, New York, 1988.

For standardization of color sets, the CIE (Commission Internationale d'Eclairage) set up hypothetical primaries XYZ, which is referred to as CIRXYZ. The resulting color representation is that all visible colors are in the positive octant, in the integration of matching functions being equal, and in the Y function matching the luminance efficiency function. Although the color specification in the CIEXYZ color space is useful color reproduction, it is not useful for evaluating relative color changes in real color space or human perception of color contrast. Therefore, other alternative color schemes have been developed such as L*u*v* and L*a*b* [13,14]. One effective approach was proposed by Mayer. G. W. Mayer, "Wavelength Selection for Synthetic Image Generation," *Computer Vision, Graphics, and Image Processing,* vol. 41, pp. 57–79. He examined the sensitivity of the visual system and derived a set of color axes that pass through the regions where the tristimulus are most likely to occur. He calls this coordinate system the $AC_1C_2$ space. The $AC_1C_2$ color space was adapted for the example color contrast computation.

For actual computation of the $AC_1C_2$ color space, RGB is first converted to CIEXYZ by the following relation, $$\begin{bmatrix} X \\ Y \\ Z \end{bmatrix} = \begin{bmatrix} 0.412453 & 0.357580 & 0.180423 \\ 0.212671 & 0.715160 & 0.072169 \\ 0.019334 & 0.119193 & 0.950227 \end{bmatrix} \begin{bmatrix} R \\ G \\ B \end{bmatrix} \quad \text{(Eq. 32)}$$

Next, the $AC_1C_2$ color space is derived using the following relation:

$$\begin{bmatrix} A \\ C_1 \\ C_2 \end{bmatrix} = \begin{bmatrix} -0.0177 & 1.0090 & 0.0073 \\ -1.5370 & 1.0821 & 0.3209 \\ 0.1946 & -0.2045 & 0.5264 \end{bmatrix} \begin{bmatrix} X \\ Y \\ Z \end{bmatrix} \quad \text{(Eq. 33)}$$

With the color conversion to the $AC_1C_2$ color space, color contrasts of objects can be computed using the geometrical distance in the color space, since the color space is now converted into a space where human perception of color contrast can be uniformly evaluated. Let a 3×3 segment or pixels of an image be denoted as:

$P_1 \quad P_2 \quad P_3$ $P_4 \quad P_5 \quad P_6$ $P_7 \quad P_8 \quad P_9$ where Pi denotes a vector of the three color components at segment location i. Then, one simple way of computing the point contrast in all directions at the center location 5 is:

$$C_5 = \frac{1}{4}|(P_1 + 2P_2 + P_3) - (P_7 + 2P_8 + P_9)| + \quad \text{(Eq. 34)}$$
$$\frac{1}{4}|(P_1 + 2P_4 + P_7) - (P_3 + 2P_2 + P_9)|$$

Another alternative is, $$C_5 = \frac{1}{4}(|P_1 - P_2| + |P_2 - P_8| + |P_3 - P_7| + |P_4 - P_6|) \quad \text{(Eq. 35)}$$

Yet, another alternative is, $$C_5 = \frac{1}{2}|P_1 - P_9| + \frac{1}{2}|P_3 - P_7| \quad \text{(Eq. 36)}$$

where $|P_i - P_j|$ denotes Euclidian norm of two vectors. It should be noted that $P_i$ can be a pixel value at the finest scale, but such fine scale is not recommended. The $P_i$ should represent a small segment depending on the resolution of the image. For example, we may select four pixels as the basis segment and represent it using the average. This approach was used as the actual experiments. One more implication of the contrasts defined in Eqs. 23–25 is that the values computed also represent a measure of edges in the image. R. C. Gonzalez and R. E. Woods, *Digital Image Processing,* Addison-Wesley Publishing Company, Reading, Mass., 1993; E. L. Hall, *Computer Image Processing and Recognition,* Academic Press, London, UK, 1979. It means that the computation of VI inherently represents the degree of sharpness of the image, which is one of the desirable characteristics.

Selection of Region For RV Computation

Figure 22:
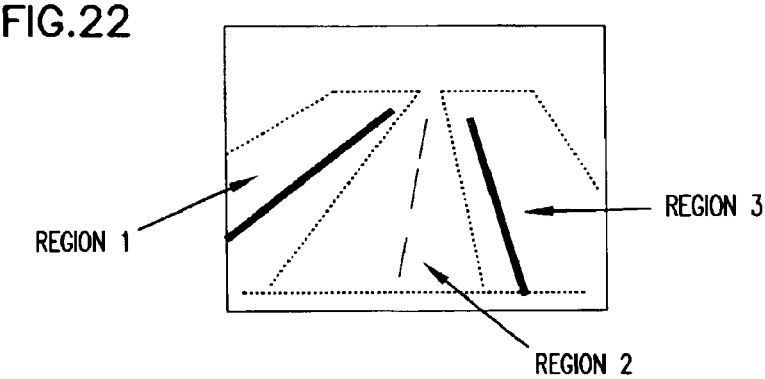
FIG. 22 is a schematic showing region selection of regions of an image of a highway.

This section describes how to select a good region from the image through an example of highway. A typical highway scene projected onto CCD by a forward-looking camera may be divided into three regions as shown in FIG. 22. In this example, two-lane one directional highway was illustrated. Regions 1 and 3 represent the left and right shoulder side of the road, respectively; and Region 2 represents the driving lanes. In Region 2, the number of vehicles on the lanes can significantly affect VI instead of visual conditions or weather conditions. As a result, VI computation could easily lead to false readings by the differences of number of vehicles on the road or not. Regions 1 and 3 are more stable in terms of object variability over time, such that visual information is more likely influenced by the atmospheric conditions. In particular, Region 3 has a better property in terms of distance information, because it shows wide range of objects from near distances to far distances. Therefore, VI should only be computed using Region 3 for better results.

Flat Surface Model for Distance Estimation

As shown in Eq. 28, distance information to each pixel or region is important for indicator computation. In general, it does not need accurate distance information, but some approximation to account the distance effect. Although when images are recorded, the distance or depth information is lost, a rough estimate of distance could be computed if the region of measuring is assumed approximately flat, because projection of flat surface to 2D data can be restored. The following computation shows estimation of distances based on a flat surface model for a camera with a known focal length.

For convenience of description, we first define the symbols used:

$L_h$: Camera lens height from the ground
CCD Size:

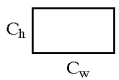

Figure 23:
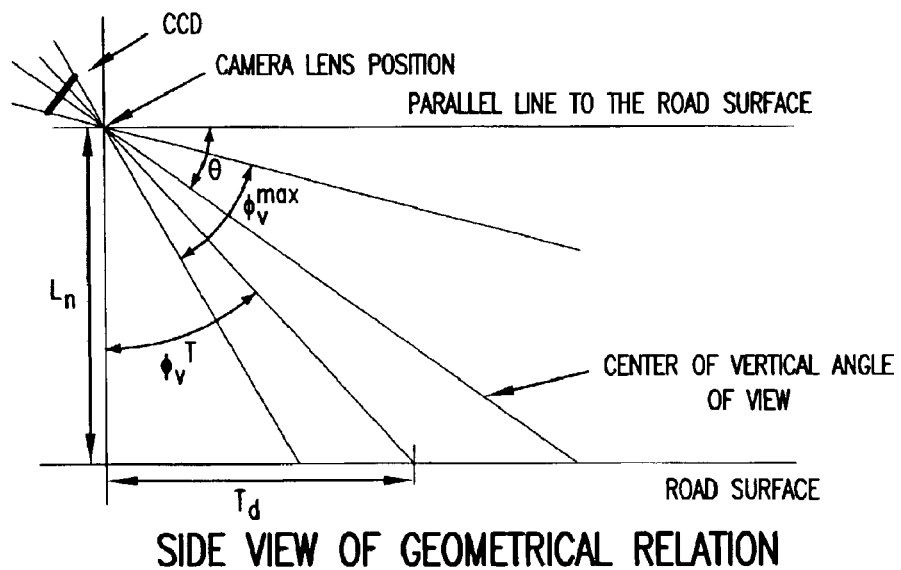
FIG. 23 is a side view showing the geometrical relation of a camera with respect to a roadway.

$f$: Camera focal length
$\phi_v^{max}$: Camera vertical angle of view
$\phi_h^{max}$: Camera horizontal angle of view
$(P_x, P_y)$: Pixel x and y position, the lower left corner is $(0,0)$
$(P_x^{max}, P_y^{max})$: Bound of pixel (x,y) position, the upper right corner.
$T_d$: Horizontal distance to target
$\phi_v^T$: The angle from the vertical line to the target
$\phi_v^{lower}$: Lower bound of the vertical angle of view expressed in relation to the vertical line
$\phi_v^{Upper}$: Upper bound of the vertical angle of view expressed in relation to the vertical line
$T_{cd}$: Parallel line distance from the camera lens to the centerline point that meets with the perpendicular line drawn from an object
$T_{dd}$: Direct line distance from the camera lens to an object
$T_{pd}$: Perpendicular line distance from the centerline to an object
$\phi_h^T$: Horizontal angle from the centerline to an object Consider that a camera with a CCD size of $(C_h \times C_w)$ is mounted at a fixed height $L_h$ and inclined towards the road with the degree of $\theta$. It is assumed that the camera does not have left or right tilt, such that the lower side of CCD is parallel to the ground level. A target is assumed located at the horizontal distance $T_d$ from the vertical line. This setup is illustrated in FIG. 23.

Horizontal and vertical angles of view of the camera follow a simple trigonometric relation:

$$\phi_v^{max} = \tan^{-1}(C_h/f) \quad \text{(Eq. 37)}$$

$$\phi_h^{max} = \tan^{-1}(C_w/f) \quad \text{(Eq. 38)}$$

The lower and upper bound of the vertical angle of view expressed in relation to the vertical line are then expressed as:

$$\phi_v^{Lower} = (90° - \theta) - \phi_v^{max}/2 \quad \text{(Eq. 39)}$$

$$\phi_v^{Upper} = (90° - \theta) + \phi_v^{max}/2 \quad \text{(Eq. 40)}$$

The vertical pixel position of the target is then computed by, $$P_y = \frac{\phi_v^T - \phi_v^{Lower}}{\phi_v^{max}} P_y^{max} \quad \text{(Eq. 41)}$$

This relation provides an estimate of y-axis position on the CCD for the target position projected on to the CCD. See FIG. 23.

Figure 24:
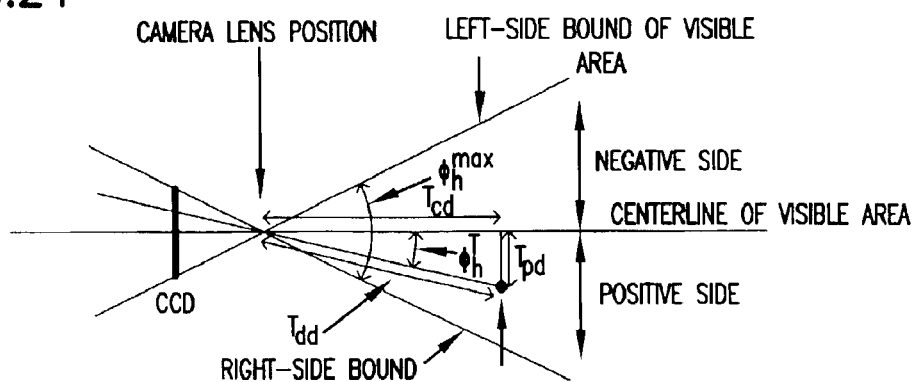
FIG. 24 is a top view showing the geometrical relation of objects with respect to a camera.

Next, in order to find the mapping point to the x-axis of the CCD the top view of the geometrical relation is considered, as illustrated in FIG. 24. The imaging area spans along with the left and right bounds of the horizontal angle of view of the camera. To create reference points, the imaging area is split into half using the horizontal centerline. A negative sign is assigned to the left side of the angles and for the perpendicular distance from the centerline. A positive sign is assigned to the right side of the angles and for the perpendicular distances from the centerline. Thus, the centerline is used as the starting point for the both sides and has zero degrees and zero perpendicular distances along the line. FIG. 24 shows visual plot of this setup.

The parallel line distance from the camera lens to the centerline point that meets with the perpendicular line drawn from an object, $T_{cd}$, has the following relation:

$$T_{cd} = \sqrt{L_h^2 + T_d^2} \quad \text{(Eq. 42)}$$

Direct line distance from the camera lens to an object, $T_{dd}$, and the horizontal angle from the centerline to an object, $\phi_h^T$, are then computed as:

$$T_{dd} = \sqrt{T_{cd}^2 + T_{pd}^2} \quad \text{(Eq. 43)}$$

$$\phi_h^T = \tan^{-1} \frac{T_{pd}}{T_{cd}} \quad \text{(Eq. 44)}$$

Similarly to the vertical case, the horizontal pixel position of the target is obtained using the horizontal angle found, i.e., $$P_x = \left(\frac{\phi_h^T}{\phi_h^{max}} + \frac{1}{2}\right) P_x^{max} \quad \text{(Eq. 45)}$$

where all parameters are now obtainable.

Next, we wish to estimate the distance from the camera lens to an object using a pixel position (x, y).

Since $$\tan\phi_h^T = \frac{T_{dd}\sin\phi_h^T}{T_{cd}},$$

the final distance from the camera lens to the target is obtained as, $$T_{dd} = \frac{T_{cd}\tan\phi_h^T}{\sin\phi_h^T} \quad \text{(Eq. 46)}$$

$$= \frac{\sqrt{L_h^2 + (L_h\tan\phi_v^T)^2} \, \tan\phi_h^T}{\sin\phi_h^T}$$

where $$\phi_h^T = \frac{P_x - \frac{1}{2}P_x^{max}}{P_x^{max}} \phi_h^{max}$$

and $$\phi_v^T = 90° - \theta + \phi_v^{max}\left(\frac{P_y}{P_y^{max}} - \frac{1}{2}\right)$$

Notice that the final derivation in Eq. 46 is a function of all known values, i.e., pixel (x,y) position, horizontal and vertical angle of camera, and the camera angle in relation to horizontal line. Therefore, an estimate of distance from the camera lens to a target can be computed based on the pixel position in the CCD. However, it should be cautioned that these estimates are based on a perfectly flat road model with no occlusion, which rarely occur in the real world. Thus, one should accept a certain level of error in the final computed distances. Another point that must be mentioned is that human perception on distance is in a log scale like many other human perceptions. Thus, the distance computed by Eq. 46 should be implemented as a log scale in the final software coding.

The "targetless" method and system for determining visibility may be significantly more cost effective and easier to implement than the target-based system or other known visibility measurement systems. Using the algorithm disclosed herein, visibility can be accurately measured using a simple system comprising a video camera, a video digitizer, and a computing device. Importantly, with a proper setup of camera and the choice of regions, visibility may be computer without known targets. In addition, the algorithm for computing "relative visibility", which is a relative measurement of visual information in reference to an ideal visual condition of an environment, may have applications beyond those described here.

When human visual perception of visibility is considered as the basis for visibility measurement model, relative visibility more accurately represents the human perception of visibility from varying degree of differences in measuring environments. In addition, the "visibility index" method of extracting image characteristics that influence visibility conditions, from which relative visibility was derived, may also have further applications.

Verification of Visibility Measurement

The present system may also provides video images of the actual scene as a byproduct of the approach used by the present invention. These visual images can be used to verify the measured visibility by manual inspection. This verification capability using visual inspection is an important feature in critical applications. Further, the camera lens system of the video camera has basically the same structure as the lens system of a human eye. Thus, if the camera is designed in the visual spectral range of the human eye, the video images recorded are a close representation of that which can be seen by the human eye. Since the visual features (contrasting portions of the targets) are used from the images to compute visibility, a more true definition of visibility can be measured rather than a single atmospheric condition (light scattering) that is measured by SLMs. Also, video cameras are already installed and used in many applications, such as traffic monitoring and transportation applications. These video cameras can be used to generate visibility measurements to save additional cost. Lastly, a computation of visibility can be done from a remote location as long as the image signal or its digitized bit map data can be transmitted to the remote location where a computer is available.

The foregoing description has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention, except insofar as limited by the prior art.

What is claimed is:

1. A visibility measurement system comprising an image sensing device for sensing at least a first and a second image of an environment, the visibility measurement system comprising a digital conversion system that maps the image of the environment into a two-dimensional data array, and a processor that computes a benchmark visibility index as a summation of measurable visual characteristics that influence visibility under a benchmark environmental condition, computes a second visibility index for a second environmental condition, and computes a relative visibility value as the ratio of the second visibility index to the benchmark visibility index.

2. The visibility measurement system of claim 1 wherein the visibility index is a function related to clarity of objects in the image, the average luminance of the image, and the average contrast of the image.

3. The visibility measurement system of claim 1 wherein the relationship between the visibility index and the average contrast of the image is defined by an approximately parabolic function.

4. The visibility measurement system of claim 1 wherein the relationship between the visibility index and the average luminance of the image is defined by an approximately parabolic function.

5. The visibility measurement system of claim 1 wherein the processor identifies a region in the image that has objects which have a uniform distance from the sensing device in the first image and in the second image, and wherein the processor computes the visibility indexes and the relative visibility value based upon the data in the region.

6. A method for computing visibility comprising:

sensing with a sensing device a benchmark image of an environment under a benchmark condition with a sensing device;

sensing with the sensing device a second image of an environment under a second condition;

computing a benchmark visibility index from the benchmark image as a summation of measurable visual characteristics that influence visibility;

computing a second visibility index from the second image as a summation of measurable visual characteristics that influence visibility;

computing a relative visibility value as the ratio of the second visibility index to the benchmark visibility index.

7. The method of claim 6 further comprising mapping the benchmark image of the environment into a two-dimensional data array before computing the benchmark visibility index.

8. The method of claim 6 wherein one or more objects are included in both the benchmark image and the second image.

9. The method of claim 8 wherein the steps of sensing a benchmark image and sensing a second image involve a sensing device, the method further comprising the step of estimating the distance from the sensing device of one or more objects in the image.

10. The method of claim 9 further comprising identifying a region in the image that includes objects having a uniform distance from the sensing device over time.

11. The method of claim 6 wherein the steps of computing a benchmark visibility index and a second visibility index involve computation of a function relating the clarity of aspects of the image, the average luminance of the image, and the average contrast of the image.

12. The method of claim 11 wherein the relationship between the visibility index and the average contrast of the image is defined by a parabolic function.

13. The method of claim 11 wherein the relationship between the visibility index and the average luminance of the image is defined by a parabolic function.

14. The method of claim 6 further comprising computing visibility based upon a logarithmic relationship between visibility and relative visibility.

15. A relative visibility measurement system comprising:
means for sensing an image of an environment;
means for identifying a region in the image that has a uniform distance from the sensing device over time;
means for computing a benchmark visibility index for the region as a summation of measurable visual characteristics that influence visibility in the region under a benchmark environmental condition;
means for computing a second visibility index for a second environmental condition;
means for computing the relative visibility in terms of the magnitude of the second visibility index in relation to the benchmark visibility index.

16. A relative visibility measurement system comprising:
an image sensing device for sensing an image of an environment;
a code segment for identifying a region in the image that has a uniform distance from the sensing device over time;
a code segment for computing a benchmark visibility index for the region as a summation of measurable visual characteristics that influence visibility in the region under a benchmark environmental condition;
a code segment for computing a second visibility index for a second environmental condition; and
a code segment for computing the relative visibility in terms of the magnitude of the second visibility index in relation to the benchmark visibility index.

17. A system for measuring relative visibility, comprising:
a video camera that is positioned to perceive a scene including objects located at various distances from the camera, the video camera providing an output comprising an image of the scene;
a processor that computes relative visibility by approximating the distance from the camera of objects in the image and comparing a region of the image to a corresponding region in a benchmark image to determine relative visibility.

18. The system of claim 17 wherein the benchmark image corresponds to 100% visibility.

19. The system of claim 17 wherein the camera is positioned such that horizon is visible from the camera view.

20. The system of claim 17 wherein the processor computes relative visibility based upon the reduction of edge information and contrast trends in the region.

21. The system of claim 17 wherein the processor computes a visibility index for the region of the image, the visibility index being a function of the clarity of objects in the image, the average luminance of the image, and the average contrast of the image.

22. The system of claim 17 wherein the relative visibility is computed as the ratio of the visibility index for a given image to the visibility index for the benchmark image.

* * * * *